US008822526B2

(12) United States Patent
Rathos et al.

(10) Patent No.: US 8,822,526 B2
(45) Date of Patent: Sep. 2, 2014

(54) SYNERGISTIC PHARMACEUTICAL COMBINATION FOR THE TREATMENT OF CANCER

(75) Inventors: Maggie Rathos, Mumbai (IN); Kalpana Joshi, Mumbai (IN); Harshal Khanwalkar, Mumbai (IN); Somesh Sharma, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 258 days.

(21) Appl. No.: 12/600,019

(22) PCT Filed: May 15, 2007

(86) PCT No.: PCT/IB2007/051841
§ 371 (c)(1),
(2), (4) Date: Nov. 13, 2009

(87) PCT Pub. No.: WO2008/139271
PCT Pub. Date: Nov. 20, 2008

(65) Prior Publication Data
US 2010/0305057 A1 Dec. 2, 2010

(51) Int. Cl.
*A01N 43/36* (2006.01)
*A61K 31/40* (2006.01)
*C07D 405/00* (2006.01)
*C07D 409/00* (2006.01)
*A61K 31/704* (2006.01)
*A61K 31/4025* (2006.01)
*A61K 31/7068* (2006.01)
*A61K 31/337* (2006.01)
*A61K 45/06* (2006.01)

(52) U.S. Cl.
CPC ........... *A61K 31/704* (2013.01); *A61K 31/4025* (2013.01); *A61K 31/7068* (2013.01); *A61K 31/337* (2013.01); *A61K 45/06* (2013.01)
USPC ............................ 514/422; 548/525; 548/532

(58) Field of Classification Search
None
See application file for complete search history.

(56) References Cited

U.S. PATENT DOCUMENTS

| | | | |
|---|---|---|---|
| 7,271,193 B2 | 9/2007 | Lal et al. | |
| 7,915,301 B2 * | 3/2011 | Lal et al. | 514/422 |
| 2005/0176696 A1 * | 8/2005 | Dorr et al. | 514/183 |
| 2005/0267066 A1 * | 12/2005 | Gianella-Borradori | 514/49 |
| 2006/0247305 A1 | 11/2006 | Wang et al. | |
| 2007/0015802 A1 | 1/2007 | Lal et al. | |

FOREIGN PATENT DOCUMENTS

WO    WO 2004/004632    *   1/2004

OTHER PUBLICATIONS

Vippagunta et al. (Adv. Drug. Deliv. Rev, 48: 3-26, 2001).*

* cited by examiner

*Primary Examiner* — Anna Pagonakis
(74) *Attorney, Agent, or Firm* — Frommer Lawrence & Haug LLP

(57) ABSTRACT

A novel pharmaceutical combination comprising a cytotoxic antineoplastic agent selected from a the group consisting of paclitaxel, docetaxel, doxorubicin and gemcitabine or a pharmaceutically acceptable salt thereof and at least one cyclin dependent kinase (CDK) inhibitor; wherein the said combination exhibits synergistic effects when used in the treatment of cancer. The invention also relates to a method for the treatment of cancer, using a therapeutically effective amount of the said combination.

7 Claims, 11 Drawing Sheets

Lane 1 is untreated control;
lane 2 is 1200 nM of compound A for 96 hour;
lane 3 is 100 nM of doxorubicin alone for 24 hour;
lane 4 is the combination of doxorubicin followed by compound A.

In Figure 7a, Doxo refers to Doxorubicin

In Figure 7b, Doxo refers to Doxorubicin

In Figure 8a, Doxo refers to Doxorubicin

">" indicates doxorubicin is administered prior to compound A

In Figure 8b, Doxo refers to Doxorubicin
">" indicates doxorubicin is administered prior to compound A 1- Control
2- Compound A (1200 nM) for 96 hour
3- Doxorubicin (100 nM) for 24 hour
4- Doxorubicin > Compound A In Figure 9, ">" indicates doxorubicin is administered prior to compound A

SYNERGISTIC PHARMACEUTICAL COMBINATION FOR THE TREATMENT OF CANCER

FIELD OF THE INVENTION

The present invention relates to a novel pharmaceutical combination for the treatment of cancer wherein said combination exhibits a synergistic effect. The pharmaceutical combination comprises a cytotoxic antineoplastic agent selected from the group consisting of paclitaxel, docetaxel, doxorubicin and gemcitabine or a pharmaceutically acceptable salt thereof and at least one cyclin dependent kinase (CDK) inhibitor selected from the compounds of formula I (as described herein) or a pharmaceutically acceptable salt or a solvate thereof. The present invention also relates to a method for the treatment of cancer, which method comprises administering to a patient in need of such a treatment a therapeutically effective amount of said combination.

BACKGROUND OF THE INVENTION

Cancer is a general term used to describe diseases in which abnormal cells divide without control. Cancer cells can invade nearby tissues and can spread through the bloodstream and lymphatic system to other parts of the body. There are different types of cancers such as bladder cancer, breast cancer, colon cancer, rectal cancer, head and neck cancer, endometrial cancer, kidney (renal cell) cancer, leukemia, small cell lung cancer, non-small cell lung cancer, pancreatic cancer, prostate cancer, thyroid cancer, skin cancer, Non-Hodgkin's Lymphoma and melanoma. Currently there are many treatments available for cancer than ever before, including chemotherapy, radiation, surgery, hormonal therapy, immune therapy and gene therapy. Chemotherapy is the routinely used treatment against many types of cancer. The most widely used chemotherapeutic agents (the antineoplastic agents) include paclitaxel, docetaxel, doxorubicin, etoposide, carboplatin, cisplatin, topotecan and gemcitabine. These and other like antineoplastic agents have been successfully used for the treatment of different cancers. However, in due course of time, some cancer patients have been found to develop resistance to monotherapy involving use of such standard antineoplastic agents. Tolerance or resistance to a drug represents a major impediment to successful treatment. Such resistance is often considered as either intrinsic (i.e. present at the onset of treatment) or acquired (i.e. occurs during courses of chemotherapy). A study involving exposure of human non-small cell lung cancer cells (NCI-H460) to gradually increasing concentrations of doxorubicin reported appearance of a new cell line (NCI-H460/R) that was resistant to doxorubicin (96.2-fold) and cross-resistant to etoposide, paclitaxel, vinblastine and epirubicin (*J. Chemother.*, 2006 February; 18(1) 66-73). In another study describing prevalence of in vitro chemotherapy resistance in non-small cell lung cancer (NSCLC) tumor cultures, extreme drug resistance or intermediate drug resistance to a number of antineoplastic agents including cisplatin, doxorubicin, etoposide, gemcitabine, navelbine, paclitaxel, taxotere and topotecan has been reported (Ann. *Thorac. Surg.* 2006 February; 81(2):440-6; discussion 446-7). Gemcitabine was considered to be the most clinically active drug for the treatment of pancreatic cancer, however it failed to significantly improve the condition of pancreatic cancer patients because of the pre-existing or acquired chemo resistance of most of the tumor cells to the drug (*Oncogene* 2003 May 22; 22(21): 3243-51). Another problem observed or prevalent in the cancer treatment is the severe toxicity associated with most of the antineoplastic agents. Incidence of severe side effects such as cardiac toxicity in case of drugs like doxorubicin has been reported in *J Egypt Natl Canc Inst.* 2005 Dec_17(4)_291-300. Despite the incidence of resistance and severe toxicity associated with the conventional antineoplastic agents e.g. gemcitabine, paclitaxel, these agents will continue to be important in the cancer treatment because they have the ability to reduce tumor mass. In order to improve the response rate and prevent toxicity associated with the conventional antineoplastic agents, new therapeutic approaches are being evaluated. One such approach is directed to a protocol involving combining different anticancer agents having different biological mechanism (Jekunen et al., Br. J. Cancer, 69, 299-306 (1994); Yeh et al., Life Sciences, 54, 431-35 (1994)). An optimal combination chemotherapy protocol may result in increased therapeutic efficacy, decreased host toxicity, and minimal or delayed drug resistance. When drugs with different toxicities are combined, each drug can be used at its optimal dose, helping minimise intolerable side effects, as reported for the combination of capecitabine and docetaxel in Oncology (Williston Park). 2002 October; 16:17-22. Some of the antineoplastic agents have been found to be synergistically effective when used in combination with other anticancer agents than when used as a monotherapy. For example, cyclophosphamide and 5-fluorouracil act synergistically in ovarian clear cell adenocarcinoma cells as reported in Cancer Lett. 2001 Jan. 10; 162(1):39-48. Combination chemotherapy can also be advantageously used for treating cancers in advanced stages which are difficult to treat with monotherapy, radiation or surgical treatment, for example, a combination of paclitaxel and gemcitabine has been reported for the treatment of metastatic non-small cell lung cancer (*Cancer,* 2006 Sep. 1; 107(5):1050-4).

Recently, combination of one or more standard antineoplastic agents such as paclitaxel, cisplatin etc. with a molecularly targeted anticancer agent for the treatment of cancer has been tried out to improve drug response rates and to address resistance to the antineoplastic agents. Molecularly targeted agents e.g. imatinib mesylate, flavopiridol etc. modulate proteins such as kinases whose activities are more specifically associated with cancerous cells. Researches over a long period of time have proven that the members of the cyclin-dependent kinase (CDK) family play key roles in various cellular processes. There are 11 members of the CDK family known till now. Among these, CDK1, 2, 3, 4, and 6 are known to play important roles in the cell cycle (Cyclins and cyclin-dependent kinases: theme and variations. *Adv Cancer Res.* 1995; 66:181-212). CDKs are activated by forming non-covalent complexes with cyclins such as A-, B-, C-, D- (D1, D2, and D3), and E-type cyclins. Each isozyme of this family is responsible for particular aspects (cell signaling, transcription, etc) of the cell cycle, and some of the CDK isozymes are specific to certain kinds of tissues. Aberrant expression and overexpression of these kinases are evidenced in many disease conditions. A number of compounds having potentially useful CDK inhibitory properties have been developed and reported in the literature. Flavopiridol is the first potent inhibitor of cyclin-dependent kinases (CDKs) to reach clinical trial. Flavopiridol has been found to potentiate synergistically the cytotoxic response of the conventional antineoplastic agents in a variety of cancer cell-lines. For example, sequential treatment of HCT116 colon cancer with docetaxel, flavopiridol and 5-fluorouracil has been reported in Acta Pharmacol Sin. 2006 October; 27(10):1375-81. Also, combined docetaxel and flavopiridol treatment for lung cancer cells has been reported in Radiother Oncol. 2004 May; 71(2): 213-21 and for treatment of gastric cancer in Mol Cancer Ther. 2003 June; 2(6):549-55.

Although combinations of anticancer agents have been proven to have a significant advance in cancer treatment protocols, there are still several unmet needs and room for improvements for medications for the treatment of cancers, which are difficult to treat, or which have shown resistance to treatment with the conventional antineoplastic agents as a monotherapy. More particularly, the development of novel combination approach for delivering known anticancer agents having different mechanism of action would represent an important advance in the art. Although the protocol involving combination of anticancer agents having different mechanism of action may work in case of some combinations, it may not work in the same manner for other combination of anticancer agents and such combination may not always result in a combination having advantageous therapeutic effects. However, the present inventors have surprisingly found that a novel pharmaceutical combination of known anticancer agents comprising a cyclin dependant kinase inhibitor selected from compounds represented by formula I (as described herein) and a standard cytotoxic antineoplastic agent for the treatment of different cancers provides unexpectedly greater efficacy than when the anticancer agents are used alone.

SUMMARY OF THE INVENTION

In one aspect, the present invention relates to a novel pharmaceutical combination comprising a cytotoxic antineoplastic agent selected from the group consisting of paclitaxel, docetaxel, doxorubicin and gemcitabine or a pharmaceutically acceptable salt thereof; and a cyclin dependent kinase (CDK) inhibitor selected from the compounds of formula I (as described herein) or a pharmaceutically acceptable salt or a solvate thereof; wherein said combination exhibits synergistic effect in the treatment of cancers.

In another aspect, the present invention relates to a pharmaceutical combination comprising a cytotoxic antineoplastic agent selected from the group consisting of paclitaxel, docetaxel, doxorubicin or and gemcitabine or a pharmaceutically acceptable salt thereof; and a cyclin dependent kinase (CDK) inhibitor selected from the compounds of formula I (as described herein) or a pharmaceutically acceptable salt or a solvate thereof, for simultaneous or sequential administration for the treatment of cancer.

In a further aspect, the present invention relates to use of the novel pharmaceutical combination for the treatment of cancer and for inducing cellular apoptosis.

In another further aspect, the present invention relates to a method of treating cancer, which method comprises administering to a patient in need thereof a therapeutically effective amount of a cytotoxic antineoplastic agent selected from the group consisting of paclitaxel, docetaxel, doxorubicin or and gemcitabine or a pharmaceutically acceptable salt thereof; in combination with a therapeutically effective amount of a cyclin dependent kinase (CDK) inhibitor selected from the compounds of formula I (as described herein) or a pharmaceutically acceptable salt or a solvate thereof.

In yet another further aspect, the present invention relates to use of the novel combination for the preparation of a medicament for treating cancer.

Other aspects and further scope of applicability of the present invention will become apparent from the detailed description to follow.

DETAILED DESCRIPTION OF THE INVENTION

Figure 1:
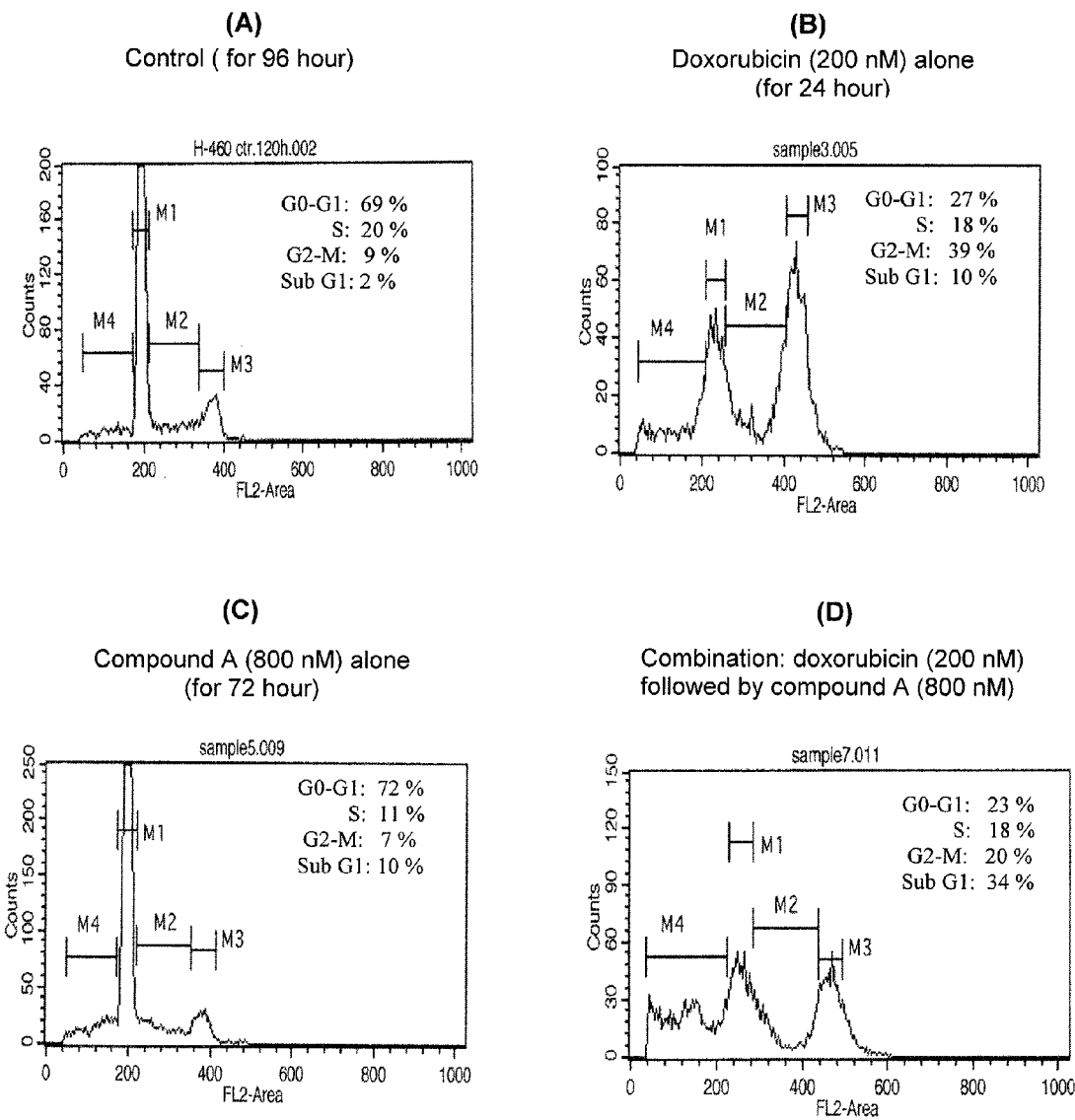
FIG. 1 illustrates that the combination of doxorubicin and the compound A in the treatment of H-460 non-small cell lung cells in vitro exhibits synergism. Graph(s) A, B, C and D represent(s) cell cycle distribution of different treatment groups namely the control (for 96 hours), 200 nM of doxorubicin alone (for 24 hours), 800 nM of the compound A alone (for 72 hours) and the combination comprising administration of 200 nM of doxorubicin (for 24 hours) followed by 800 nM of compound A (72 hours) respectively.

It has now been found that the novel combination of the present invention, which comprises a conventional cytotoxic antineoplastic agent selected from the group consisting of paclitaxel, docetaxel, doxorubicin and gemcitabine or a pharmaceutically acceptable salt thereof and a CDK inhibitor selected from the compounds of formula I (as described herein) or a pharmaceutically acceptable salt or a solvate thereof; exhibit synergistic effect when used in the treatment of cancer, particularly solid tumors.

The CDK inhibitor used in the pharmaceutical combination of the present invention is selected from the compounds of formula I as described herein below. The CDK inhibitors represented by the following formula I are disclosed in PCT Patent Publication No. WO2004004632. The compounds of formula I are promising CDK inhibitors, which can inhibit proliferation of many cancer cells. The compounds of formula I as used in the present invention are effective against various solid and haematological malignancies. The inventors of the present invention observed that combining CDK inhibitors of formula I with a conventional cytotoxic antineoplastic agent selected from the group consisting of paclitaxel, docetaxel, doxorubicin OF and gemcitabine resulted in an increase in apoptosis, or programmed cell death.

The CDK inhibitors used in the present invention are selected from the compounds represented by the following formula I,

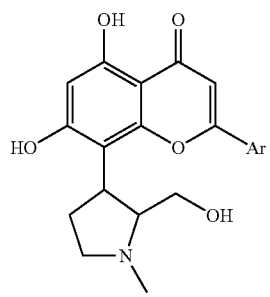

Formula I wherein Ar is a phenyl group, which is unsubstituted or substituted by 1, 2, or 3 identical or different substituents selected from: halogen such as chloro, bromo, fluoro or iodo, nitro, cyano, $C_1$-$C_4$-alkyl, trifluoromethyl, hydroxyl, $C_1$-$C_4$-alkoxy, carboxy, $C_1$-$C_4$-alkoxycarbonyl, $CONH_2$, and $NR_1R_2$;
wherein $R_1$ and $R_2$ are each independently selected from hydrogen or $C_1$-$C_4$-alkyl.

The manufacture of the compounds of formula I, which may be in the form of pharmaceutically acceptable salts and solvates, and the manufacture of oral and/or parenteral pharmaceutical composition containing the above compounds are disclosed in PCT Patent Publication No. WO2004004632. This patent, which is incorporated herein by reference, discloses that the CDK inhibitors represented by formula I exhibit significant anticancer efficacy.

As indicated herein above the CDK inhibitors of formula I may be used in the form of their salts or solvates. Preferred salt of compounds of formula I include hydrochloride salt, methanesulfonic acid salt and trifluoroacetic acid salt.

It will be appreciated by those skilled in the art that the compounds of formula I contain at least two chiral centers. The compounds of formula I thus exist in the form of two different optical isomers (i.e. (+) or (−) enantiomers). All such enantiomers and mixtures thereof including racemic mixtures are included within the scope of the invention. The enantiomers of the compound of formula I can be obtained by methods disclosed in PCT Application Publication Nos. WO2004004632 and WO2007148158, which patent applications are incorporated herein by reference in their entirety. The enantiomers of the compound of formula I can also be obtained by methods well known in the art, such as chiral HPLC and enzymatic resolution. Alternatively, the enantiomers of the compounds of formula (I) can be synthesized by using optically active starting materials. Thus, the definition of the CDK inhibitor of formula I is inclusive of all possible stereoisomers and their mixtures. The formula I definition includes the racemic forms and the isolated optical isomers having the specified activity.

The conventional cytotoxic antineoplastic agent(s) used in the novel pharmaceutical combination of the present invention may be selected from the group consisting of paclitaxel, docetaxel, doxorubicin, gemcitabine and analogous cytotoxic antineoplastic agents which exhibit the anti-cancer activity through similar mechanism of action.

Paclitaxel is a natural diterpene product isolated from the Pacific yew tree *Taxus brevifolia* (Rowinsky et. al., J. Natl. Cancer Inst., 82, 1247-1259 (1990)). Isolation of paclitaxel and its structure is disclosed in J. Am. Chem. Soc. 93, 2325 (1971). It is an antimicrotubule agent that promotes the assembly of microtubules from tubulin dimers and stabilizes microtubules by preventing depolymerization. Paclitaxel has been approved for clinical use in the treatment of ovarian cancer (Merkman et al.; Yale Journal Of Biology and Medicine, 64:583, 1991) and for the treatment of breast cancer (Holmes et al; J. Nat. cancer Inst., 83; 1797, 1991), however, it is also useful in treating other cancers for example, it has been considered as a potential candidate for the treatment of head and neck cancer (Forastire et. al., Sem. Oncol., 20: 56, 1990) and lung cancer (M. Ghaemmaghami et al; Chest; 113; 86-91 (1998)). Paclitaxel is disclosed in U.S. Pat. No. 5,670,537 which is incorporated herein by reference for its teaching on the use or administration of paclitaxel in the treatment of susceptible cancers. Paclitaxel is commercially available as an injectable solution, Taxol®. Use of paclitaxel as monotherapy is generally accompanied by undesirable side effects, including hypersensitivity reactions, hypotension, bradycardia, hypertension, nausea and vomiting, and injection site reactions.

Docetaxel belongs to the taxane family and is a semi-synthetic derivative of paclitaxel. Docetaxel is indicated primarily for breast cancer and non-small cell lung cancer. It is also useful in treating other cancers. This compound is disclosed in U.S. Pat. No. 4,814,470, which is incorporated herein by reference for its teaching of the synthesis and use of docetaxel for treating susceptible cancers. Docetaxel trihydrate is commercially available as an injectable solution, Taxotere®. All treatments based on taxoid derivatives, including docetaxel, can show serious and troubling toxicities, such as myelosuppression, neutropenia, hypersensitivity, peripheral neuropathy, and fluid retention, among others (Fumoleau et al., *Bull. Cancer*, (82)8: 629-636 (1995)).

Doxorubicin is the generic name for Adriamycin® and is commercially available in an injectable form. Doxorubicin was first isolated from the fermentation broth of *Sreptomyces peucetius* var *caesius* (U.S. Pat. No. 3,590,028). This cytotoxic antineoplastic agent binds to nucleic acids, presumably by specific intercalation of the planar anthracycline nucleus with the DNA double helix, resulting in abnormal cellular replication. Doxorubicin is used in the treatment of breast, bladder, liver, lung, prostate, stomach and thyroid cancers; bone and soft tissue sarcomas; lymphomas and leukemias; and tumors of childhood. Use of doxorubicin is generally accompanied by several side effects including myelosuppression, nausea and vomiting, mucocutaneous, and cardiac effects.

Gemcitabine is the generic name assigned to 2'-deoxy-2',2'-difluorocytidine. It is commercially available as the monohydrochloride salt, and as the β-isomer. Gemcitabine is disclosed in U.S. Pat. Nos. 4,808,614 and 5,464,826, which are incorporated herein by reference for their teaching of how to synthesize and use gemcitabine for treating susceptible cancers. The commercial formulation of gemcitabine hydrochloride as a single agent is indicated as first-line treatment for patients with locally advanced or metastatic adenocarcinoma of the pancreas or lung cell carcinoma (NSCLC), and is commonly used in patients previously treated with 5-fluorouracil.

The general terms used hereinbefore and hereinafter preferably have within the context of this disclosure the following meanings, unless otherwise indicated: The singular forms "a," "an," and "the" include plural reference unless the context clearly dictates otherwise.

The term "an antineoplastic agent" is synonymous to "a chemotherapeutic agent" or "an anticancer agent" and refers to a therapeutic agent, which acts by inhibiting or preventing the growth of neoplasms. The term "an antineoplastic agent" or "an anticancer agent" in general refers to compounds that prevent cancer cells from multiplying (i.e. anti-proliferative agents). In general, the antineoplastic agent(s) fall into two classes, anti-proliferative cytotoxic and anti-proliferative cytostatic. Cytotoxic agents prevent cancer cells from multiplying by: (1) interfering with the cell's ability to replicate DNA and (2) inducing cell death and/or apoptosis in the cancer cells. Anti-proliferative cytostatic agents act via modulating, interfering or inhibiting the processes of cellular signal transduction which regulate cell proliferation. In the present invention the antineoplastic agents comprised in the pharmaceutical combination of the present invention are the cytotoxic agents and hence are referred to as cytotoxic antineoplastic agents.

As used herein, the term "synergistic" means that the effect achieved with the methods and combinations of this invention is greater than the sum of the effects that result from using the cytotoxic antineoplastic agent(s) or a pharmaceutically acceptable salt thereof, and CDK inhibitor of formula I or a pharmaceutically acceptable salt or a solvate thereof, separately. Advantageously, such synergy provides greater efficacy at the same doses, and/or prevents or delays the build-up of multi-drug resistance.

As used herein the term "therapeutically effective amount" refers to an amount of chemotherapeutic agent, which provides the maximum apoptosis of proliferative cells at the least toxicity to non-proliferative cells.

The term "apoptosis" refers to a type of cell death in which a series of molecular steps in a cell leads to its death. This is the body's normal way of getting rid of unneeded or abnormal cells. The process of apoptosis may be blocked in cancer cells. Also called programmed cell death. (Dictionary of cancer terms. National Cancer Institute)

As used herein the term "increasing apoptosis" is defined as an increase in the rate of programmed cell death, i.e. more cells are induced into the death process as compared to exposure (contact) with either the cytotoxic antineoplastic agent alone or the CDK inhibitor alone.

The term "subject" as used herein, refers to an animal, preferably a mammal, most preferably a human, who has been the object of treatment, observation or experiment.

In one embodiment, the present invention relates to a novel pharmaceutical combination for the treatment of cancer wherein said combination comprises a cytotoxic antineoplastic agent selected from the group consisting of paclitaxel, docetaxel, doxorubicin or gemcitabine or a pharmaceutically acceptable salt thereof and at least one cyclin dependent kinase (CDK) inhibitor selected from the compounds of formula I (as described herein) or a pharmaceutically acceptable salt or a solvate thereof.

In one embodiment, the pharmaceutical combination comprising the CDK inhibitor of formula I and the cytotoxic antineoplastic agents as described herein, is not exclusively limited to those combinations which are obtained by physical association of said ingredients, but also encompass those which permit a separate administration, which can be simultaneous, sequential or spaced out over a period of time so as to obtain maximum efficacy of the combination. Thus, the pharmaceutical combination may be administered simultaneously or spaced out over a period of time for an effective cancer treatment.

For the purpose of the present invention, the CDK inhibitor selected from the compounds of formula I may be administered, for example, prior to, after or concurrent with the cytotoxic antineoplastic agent. In a preferred embodiment of the present invention, the cytotoxic antineoplastic agent or a pharmaceutically acceptable salt thereof, is administered prior to administration of the CDK inhibitor of formula I or a pharmaceutically acceptable salt or a solvate thereof, in the dosage range described below. However, the optimum method and sequence for administration of the CDK inhibitor and the cytotoxic antineoplastic agent under given conditions may be suitably selected by those skilled in the art by following routine techniques and the information contained in the present specification.

In one embodiment, the constituents comprised in the combination may have to be administered by different routes, because of their different physical and chemical characteristics. For example, the CDK inhibitors of Formula I may be administered either orally or parenterally to generate and maintain good blood levels thereof, while the cytotoxic antineoplastic agent(s) may be administered parenterally, by intravenous, subcutaneous or intramuscular route.

For oral use, the CDK inhibitors of formula I may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc and sugar.

For intramuscular, intraperitoneal, subcutaneous and intravenous use, sterile solutions of the active ingredient (the cytotoxic antineoplastic agent(s) or the CDK inhibitor) are usually employed, and the pH of the solutions should be suitably adjusted and buffered.

In another embodiment, the present invention relates to a method for the treatment of cancer, which method comprises administering to a subject in need of such a treatment a therapeutically effective amount of said combination. Accordingly, in the method of the present invention, cancer is treated in a subject by administering to the subject a therapeutic amount of an cytotoxic antineoplastic agent effective to treat the cancer, in combination with a therapeutically effective amount of a CDK inhibitor selected from the compounds of formula I or a pharmaceutically acceptable salt or a solvate thereof, wherein a synergistic effect results.

As indicated herein before, the active ingredients contained in the pharmaceutical composition can be administered simultaneously or sequentially.

Thus, according to the present invention, the method of treatment of cancer comprises administering to a subject in need of such treatment a therapeutic amount of the cytotoxic antineoplastic agent simultaneously with a therapeutic amount of the CDK inhibitor represented by the compounds of formula I.

In one embodiment, the method of treatment of cancer involves sequential administration of a therapeutic amount of the cytotoxic antineoplastic agent and a therapeutic amount of the CDK inhibitor represented by the compounds of formula I, to a subject in need of such treatment.

In another embodiment, the method of treatment of cancer involves administration to a subject in need of such treatment a therapeutic amount of the cytotoxic antineoplastic agent prior to administration of the CDK inhibitor represented by the compounds of formula I.

The method and the pharmaceutical combination of the present invention may be used in the treatment of cancer selected from the group comprising breast cancer, lung cancer (including small and non-small cell lung cancer and lung adenocarcinoma), ovarian cancer, pancreatic cancer (including exocrine pancreatic carcinoma), gastric cancer, colorectal cancer and hepatocellular carcinoma.

In a preferred embodiment, the pharmaceutical combination of the present invention can be used in the treatment of cancer selected from non-small cell lung cancer and pancreatic cancer.

The actual dosage of the active ingredients contained in the combination may be varied depending upon the requirements of the patient and the severity of the condition being treated. Determination of the proper dosage for a particular situation is within the skill of the art. Generally, treatment is initiated with smaller doses, which are less than the optimum dose of the compound. Thereafter, the dose of each ingredient is increased by small amounts until the optimum effect under the circumstances is reached. However, the amount of each ingredient in the pharmaceutical combination will typically be less than an amount that would produce a therapeutic effect if administered alone. For convenience, the total daily dose may be divided and administered in portions during the day if desired. In a preferred embodiment, the cytotoxic antineoplastic agent or a pharmaceutically acceptable salt thereof, and CDK inhibitor represented by the compounds of formula I or a pharmaceutically acceptable salt or a solvate thereof are administered sequentially in injectable forms, such that the cytotoxic antineoplastic agent is administered in a synergistically effective dose ranging from 10 mg to 1400 mg, preferably ranging from 15 mg to 1000 mg and the CDK inhibitor is administered in a synergistically effective dose ranging from 5 mg to 750 mg, preferably ranging from 10 mg to 300 mg.

In one preferred embodiment of the invention, when the cytotoxic antineoplastic agent is paclitaxel, it is administered in a synergistically effective dose ranging from 30 mg to 300 mg.

In yet another preferred embodiment of the invention, when the cytotoxic antineoplastic agent is docetaxel, it is administered in a synergistically effective dose ranging from 20 mg to 175 mg.

In yet another preferred embodiment of the invention, when the cytotoxic antineoplastic agent is doxorubicin, it is administered in a synergistically effective dose ranging from 17.5 mg to 75 mg.

In yet another preferred embodiment of the invention, when the cytotoxic antineoplastic agent is gemcitabine, it is administered in a synergistically effective dose ranging from 70 mg to 1200 mg.

The combinations provided by this invention have been evaluated in certain assay systems, and in several different administration schedules in vitro. The experimental details are as provided herein below. The data presented herein clearly indicate that the cytotoxic antineoplastic agent when combined with a CDK inhibitor of formula I exhibits synergistic effect. It is clearly indicated that the anticancer agents when used in combination in the treatment of cancer increases apoptosis or cytotoxicity in proliferative cells than when the cells are treated with only the CDK inhibitor of formula I alone or the cytotoxic antineoplastic agent alone. For instance, it can be clearly observed from the data provided in the tables 2-4 that the CDK inhibitor, a representative compound of formula I designated herein as the compound A, synergistically enhanced the cytotoxicity of doxorubicin in an in vitro analysis against non-small cell lung carcinoma H-460 cells.

The representative compound, the compound A used in the pharmacological assays refers to (+)-trans-2-(2-Chloro-phenyl)-5,7-dihydroxy-8-(2-hydroxymethyl-1-methyl-pyrrolidin-3-yl)-chromen-4-one hydrochloride and was one of the compounds disclosed in the published PCT patent application WO2004004632, incorporated herein by reference.

Figure 7A:
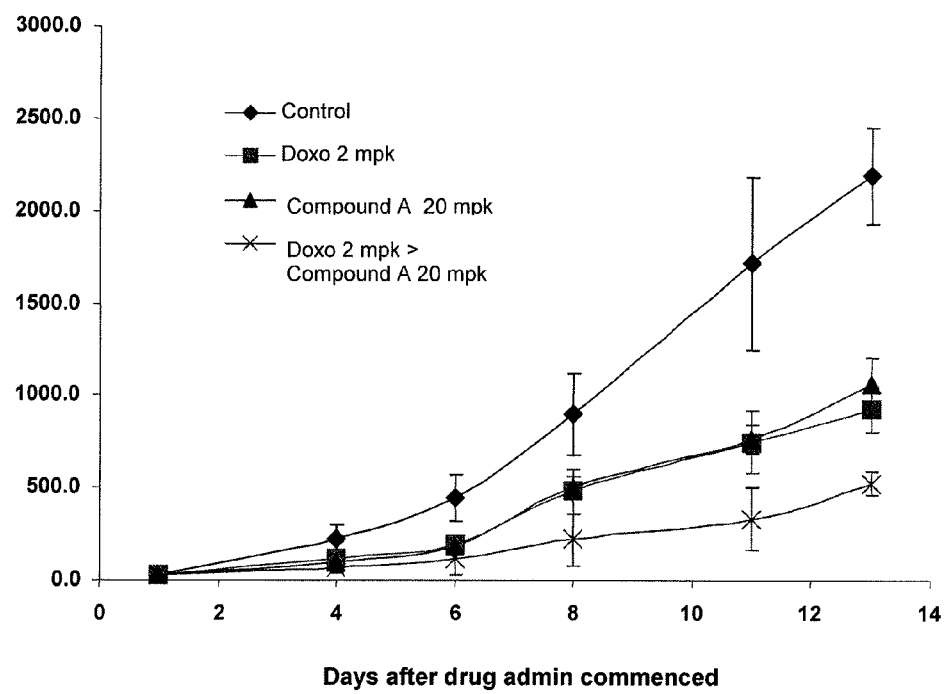
FIG. 7a illustrates in vivo efficacy of doxorubicin (2 mpk) from human non-small cell lung carcinoma (H-460) cells and compound A (20 mpk) combination in H-460 xenograft model.
Figure 7B:
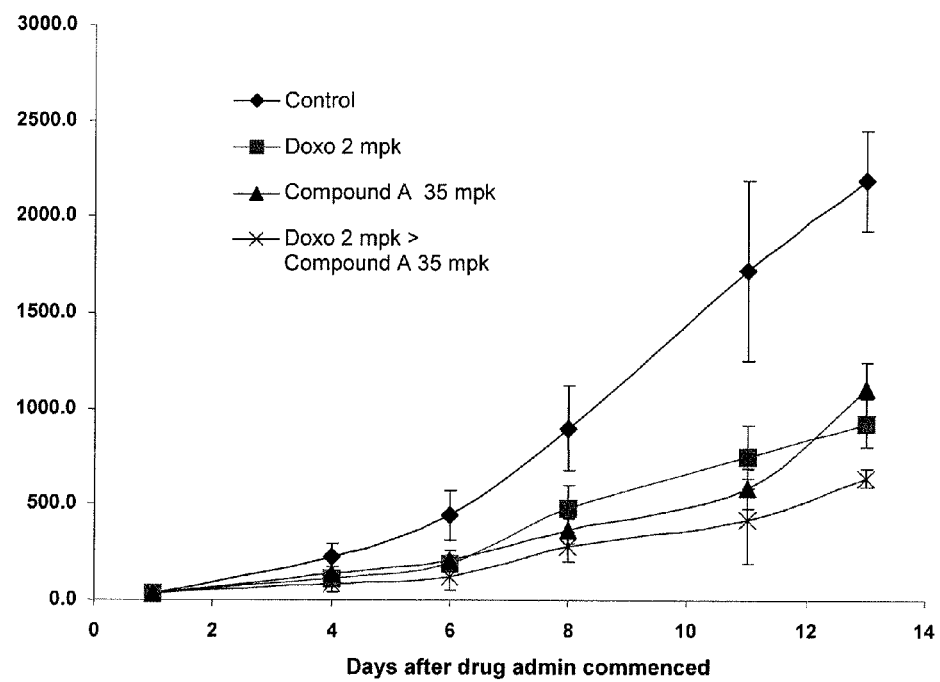
FIG. 7b illustrates in vivo efficacy of doxorubicin (2 mpk) and compound A (35 mpk) combination in H-460 xenograft model.
Figure 8A:
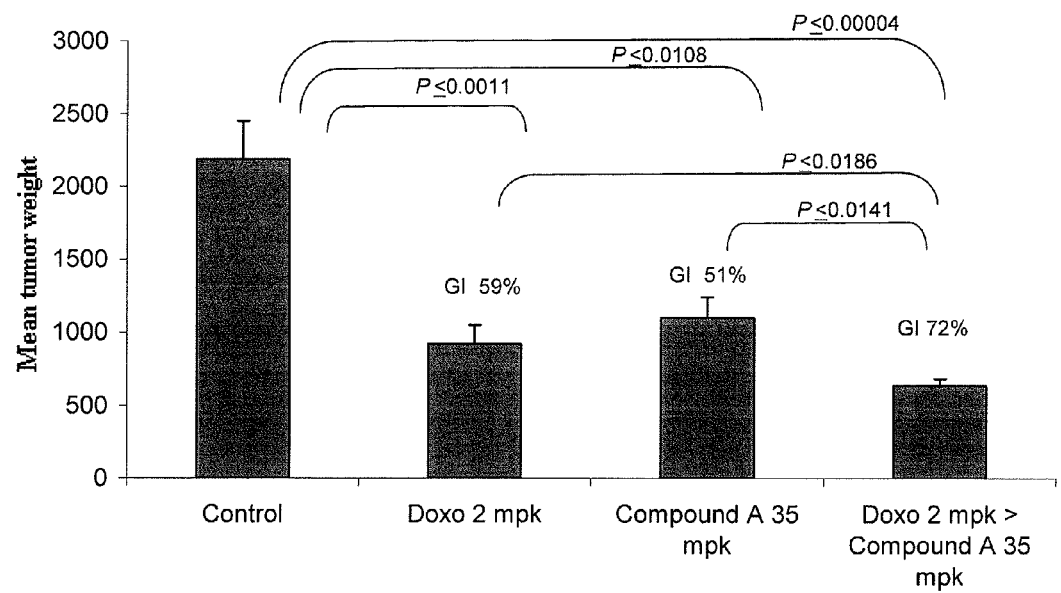
FIGS. 8a & 8b show the mean tumor weight at the end of the treatment and SE (bars) of 8 tumors from individual mouse in each group at the end of the study. Percent growth inhibition (GI) at the end of the treatment is represented for the respective group on the top of each bar. Paired t test were used to assess statistical significance of difference between different treatment groups. A statistically significant difference was considered to be present at $P<0.05$.
Figure 8B:
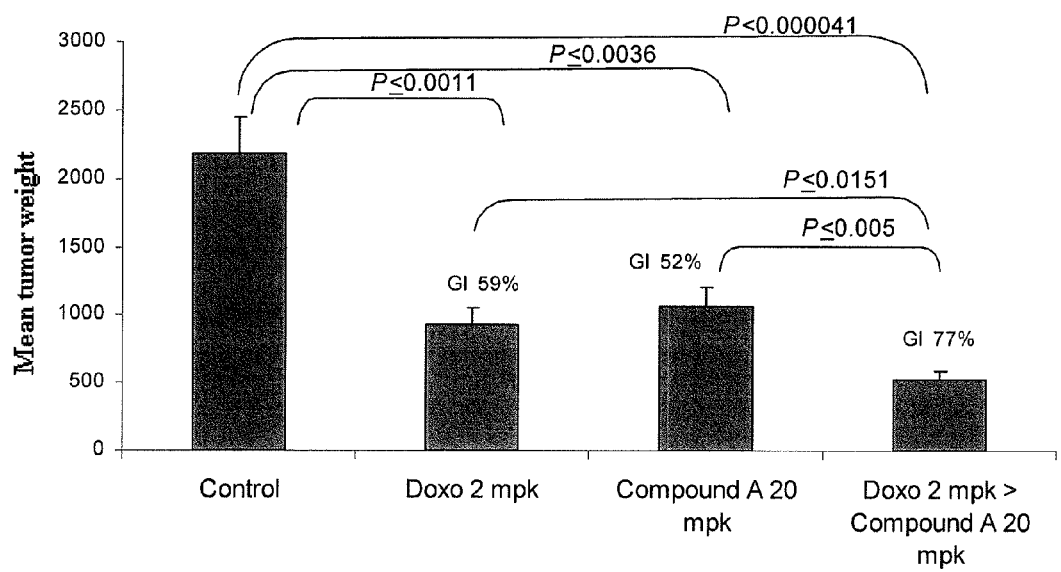

The inventors also established xenograft models to extend in vitro observations to an in vivo system. The inventors tested the combination of the present invention for its in vivo efficacy using non-small cell lung xenograft models of SCID (Severely Combined Immune Deficient) male mice. It was observed that the CDK inhibitor synergistically enhanced efficacy of doxorubicin when administered in sequential combination with doxorubicin. It is evident from the graphical presentation in FIGS. 7a and 7b that the pharmaceutical combination of the present invention exhibited therapeutically synergistic activity in non-small cell lung xenograft models of SCID mice.

In a parallel in vitro study conducted by the present inventors involving use of a combination comprising a conventional cytotoxic antineoplastic agent, doxorubicin and another known CDK inhibitor, Flavopiridol in the treatment of human non-small cell lung carcinoma H-460 cell lines, it was found that the combination of doxorubicin and flavopiridol irrespective of the sequence of administration resulted in an additive effect and no synergism was exhibited (Table 16—A, B, C). The details of this study are demonstrated herein below. Thus, it cannot be predicted with certainty that a combination of anticancer agents having different mechanism of action, may always result in advantageous therapeutic effects. However, the inventors have clearly demonstrated the synergistic efficacy of the novel pharmaceutical combination of the present invention.

The synergistic effect of the combination of the present invention comprising a cytotoxic antineoplastic agent and a CDK inhibitor is now explained in more details with reference to preferred embodiments thereof. It is to be noted that these are provided only as examples and not intended to limit the invention.

Pharmacological Assays:
In Vitro Cytotoxicity Assay:

The cytotoxicity assay used was MTS (3-(4,5-dimethylthiazol-2-yl)-5-(3-carboxymethoxyphenyl)-2-(4-sulfophenyl)-2H-tetrazolium, inner salt) assay. The human non-small cell lung carcinoma H-460 cells were seeded at a density of 1500 cells/well in 180 μL of culture medium in 96-well plate and incubated overnight to allow the cells to adhere. Varying concentrations of the drugs contained in the combination were added to the wells and incubated for an appropriate period of time in humidified 5% $CO_2$ incubator at 37° C. in case of a single drug exposure. When treated with two drugs the conventional cytotoxic antineoplastic agent (paclitaxel, docetaxel and doxorubicin) was administered for 3 hours or 24 hours followed by removal of the medium and washing of the cells once with the medium. After washing the cells, two different concentrations of compound A was added to the wells and the plates were incubated for 48, 72 or 96 hours in humidified 5% $CO_2$ incubator at 37° C. Control wells were treated with a vehicle. At the end of the incubation period, the medium was removed from the wells and 20 μL of MTS (2 mg/mL in phosphate buffer saline, pH 6-6.5 and filter sterilized) and 1 μL of phenazine methosulfate (PMS, 3 mM in phosphate buffered saline, pH 7.3 and filter sterilized) was added to each well and the total volume was adjusted to 200 μL with complete medium. The plate was incubated for 2-4 hours in humidified 5% $CO_2$ incubator at 37° C. The plate was read at 490 nM in a Spectrophotometer (SpectraMax, Molecular Devices); percentage cytotoxicity and $IC_{50}$ was calculated using SoftMax, software for SpectraMax.

Example 1

This example exhibits the synergistic effect of the combination of doxorubicin and compound A wherein doxorubicin and the compound A were administered sequentially such that doxorubicin was administered prior to the compound A. The human non-small cell lung carcinoma H-460 cells were seeded at a density of 1500 cells/well. The cells were first treated with either of the drugs alone i.e. with doxorubicin or the compound A alone. Doxorubicin treatment was for the first 24 hours followed by complete medium for 72 hours while in case of the compound A, the first 24 hours was in complete medium followed by the compound A for the next 72 hours. The concentrations of doxorubicin used were 100 nM and 200 nM while compound A was used at a concentration of 800 nM ($IC_{30}$ concentration after 48 hours treatment). In the combination study, the cells were first treated with 200 nM or 100 nM doxorubicin for the first 24 hours followed by 800 nM of the compound A for 72 hours. After completion of the drugs treatment i.e. at the end of 96 hours the plates were processed for MTS viability assay and the percent cytotoxicity was calculated as compared to control. The results are as shown in the following Table 1.

TABLE 1

| Drug treatment | Concentration of Doxorubicin (nM) | Concentration of CDK inhibitor (Compound A) (nM) | % Cytotoxicity |
|---|---|---|---|
| Doxorubicin | 200 | 0 | 19 |
| | 100 | 0 | 16 |
| CDK inhibitor (compound A) | 0 | 800 | 17 |
| Doxorubicin (24 hours) followed by the CDK inhibitor (compound A) (72 hours) | 200 | 800 | 53 |
| | 100 | 800 | 46 |

Example 2

This example exhibits the synergistic effect of the combination of doxorubicin and compound A wherein doxorubicin and the compound A were administered sequentially such that doxorubicin was administered prior to the compound A. In this example the compound A was used at a concentration of 1200 nM. The human non-small cell lung carcinoma H-460 cells were seeded at a density of 1500 cells/well. The cells were first treated with either of the drugs alone i.e. with doxorubicin or the compound A alone. Doxorubicin treatment was for the first 24 hours followed by complete medium for 72 hours while in case of the compound A the first 24 hours was in complete medium followed by the compound A for the next 72 hours. The concentrations of doxorubicin used were 200 nM and 100 nM, while the compound A was used at a concentration of 1200 nM ($IC_{50}$ concentration after 48 hours treatment). In the combination study, the cells were first treated with 100 nM or 200 nM doxorubicin for 24 hours followed by 1200 nM of the compound A for 72 hours. After completion of the drugs treatment i.e. at the end of 96 hours the plates were processed for MTS viability assay and the percent cytotoxicity was calculated as compared to control. The results are as shown in the following Table 2.

TABLE 2

| Drug treatment | Concentration of Doxorubicin (nM) | Concentration of CDK inhibitor (Compound A) (nM) | % Cytotoxicity |
|---|---|---|---|
| Doxorubicin | 200 | 0 | 19 |
| | 100 | 0 | 16 |
| CDK inhibitor (compound A) | 0 | 1200 | 36 |
| Doxorubicin (24 hours) followed by CDK inhibitor (compound A) (72 hours) | 200 | 1200 | 70 |
| | 100 | 1200 | 67 |

Example 3

This example exhibits the synergistic effect of the combination of doxorubicin and compound A wherein doxorubicin and the compound A were administered sequentially such that doxorubicin was administered prior to the compound A. In this example the compound A was used at a concentration of 1200 nM and the spaced out time period was 96 hours. The human non-small cell lung carcinoma H-460 cells were seeded at a density of 1500 cells/well. The cells were first treated with either of the drugs alone i.e. with doxorubicin or the compound A alone. Doxorubicin treatment was for the first 24 hours followed by complete medium for 96 hours while in case of the compound A, the first 24 hours was in complete medium followed by the compound A for the next 96 hours. The concentrations of doxorubicin used were 100 nM and 200 nM while compound A was used at a concentration of 1200 nM ($IC_{50}$ concentration after 48 hours treatment). In the combination study, the cells were first treated with 100 nM or 200 nM doxorubicin for 24 hours followed by 1200 nM of the compound A for 96 hours. After completion of the drugs treatment i.e. at the end of 120 hours the plates were processed for MTS viability assay and the percent cytotoxicity was calculated as compared to control. The results are as shown in the following Table 3.

TABLE 3

| Drug treatment | Concentration of Doxorubicin (nM) | Concentration of CDK inhibitor (Compound A) (nM) | % Cytotoxicity |
|---|---|---|---|
| Doxorubicin | 200 | 0 | 17 |
|  | 100 | 0 | 8 |
| CDK inhibitor (compound A) | 0 | 1200 | 32 |
| Doxorubicin (24 hours) followed by CDK inhibitor (compound A) (96 hours) | 200 | 1200 | 73 |
|  | 100 | 1200 | 69 |

Example 4

This example exhibits the synergistic effect of the combination of doxorubicin and compound A administered simultaneously for 120 hours. The human non-small cell lung carcinoma H-460 cells were seeded at a density of 1500 cells/well. The cells were first treated with either of the drugs alone i.e. with doxorubicin or the compound A alone for 120 hours each. The concentrations of doxorubicin used were 30 nM and 100 nM while the compound A was used at a concentration of 800 nM and 1200 nM (~$IC_{30}$ and ~$IC_{50}$ concentration after 48 hours treatment). In this combination study, 30 nM or 100 nM doxorubicin and 1200 nM or 800 nM of compound A respectively were added together for 120 hours. After completion of the drugs treatment i.e. at the end of 120 hours the plates were processed for MTS viability assay and the percent cytotoxicity was calculated as compared to control. The results are as shown in the following Table 4.

TABLE 4

| Drug treatment | Concentration of Doxorubicin (nM) | Concentration of CDK inhibitor (Compound A) (nM) | % Cytotoxicity |
|---|---|---|---|
| Doxorubicin | 100 | 0 | 19 |
|  | 30 | 0 | 3 |
| CDK inhibitor (compound A) | 0 | 1200 | 44 |
|  | 0 | 800 | 24 |
| Doxorubicin and CDK inhibitor (compound A) together for 120 hours | 100 | 800 | 61 |
|  | 30 | 1200 | 60 |

Example 5

This example shows that there is no synergistic effect when compound A was administered before the cytotoxic antineoplastic agent, doxorubicin. The human non-small cell lung carcinoma H-460 cells were seeded at a density of 1500 cells/well. The cells were first treated with either of the drugs alone i.e. with doxorubicin or the compound A alone. The compound A treatment was for the first 96 hours followed by complete medium for 24 hours while in case of doxorubicin, the first 96 hours was in complete medium followed by doxorubicin for 24 hours. The concentrations of doxorubicin used were 30 nM, 70 nM, 100 nM and 200 nM while the compound A was used at a concentration of 800 nM and 1200 nM (~$IC_{30}$ and ~$IC_{50}$ concentration after 48 hours treatment). In this combination study, 1200 nM or 800 nM of compound A was added for the first 96 hours followed by 30 nM, 70 nM, 100 nM or 200 nM of doxorubicin for 24 hours. After completion of the drugs treatment i.e. at the end of 120 hours, the plates were processed for MTS viability assay and the percent cytotoxicity was calculated as compared to control. Table 6 indicates that the percent cytotoxicity in this combination is lower than the cytotoxicity of compound A when administered alone. Therefore this sequence effect is antagonistic, as doxorubicin does not potentiate the effect of the first drug, which is the compound A in this case. The results are as shown in the following Table 5.

TABLE 5

| Concentration of doxorubicin (nM) | Concentration of CDK inhibitor (compound A) (nM) | % Cytotoxicity [CDK inhibitor compound A (96 hours) followed by Doxorubicin (24 hours)] |
|---|---|---|
| 200 | 1200 | 46 |
|  | 800 | 16 |
| 100 | 1200 | 45.6 |
|  | 800 | 15 |
| 70 | 1200 | 42.3 |
|  | 800 | 14 |
| 30 | 1200 | 41 |
|  | 800 | 17.5 |
| 0 | 1200 | 52 |
| 0 | 800 | 19 |

Examples 1-4 clearly exhibit that the CDK inhibitor synergistically potentiates the effect of doxorubicin when the CDK inhibitor is administered after or simultaneously with the cytotoxic drug. Example 5 also shows the importance of sequential treatment. Treatment with doxorubicin followed by the CDK inhibitor is found to be synergistic while the reverse sequence is not effective.

Example 6

This example exhibits the synergistic effect of the combination of docetaxel and the compound A wherein docetaxel and the compound A were administered sequentially such that docetaxel was administered prior to the compound A. The human non-small cell lung carcinoma H-460 cells were seeded at a density of 3000 cells/well. The cells were first treated with either of the drugs alone i.e. with docetaxel or the compound A alone. Docetaxel treatment was for the first 3 hours followed by complete medium for 45 hours while in case of the compound A treatment, the first 3 hours was in complete medium followed by the compound A for the next 45 hours. The concentrations of docetaxel used were 0.1 nM and 3 nM while the compound A was used at a concentration of 700 nM (~$IC_{30}$ concentration after 48 hour treatment). In this combination study, the cells were first treated with 0.1 nM or 3 nM of docetaxel for 3 hours followed by 700 nM of the compound A for 45 hours. After completion of the drugs treatment i.e. at the end of 48 hours the plates were processed for MTS viability assay and the percent cytotoxicity was calculated as compared to control. The results are as shown in the following Table 6.

TABLE 6

| Drug treatment | Concentration of Docetaxel (nM) | Concentration of CDK inhibitor (Compound A) (nM) | % Cytotoxicity |
|---|---|---|---|
| Docetaxel | 3 | 0 | 2 |
|  | 0.1 | 0 | 0 |

TABLE 6-continued

| Drug treatment | Concentration of Docetaxel (nM) | Concentration of CDK inhibitor (Compound A) (nM) | % Cytotoxicity |
|---|---|---|---|
| CDK inhibitor (compound A) | 0 | 700 | 13 |
| Docetaxel (3 hours) followed by the CDK inhibitor (compound A) (45 hours) | 3 | 700 | 33 |
| | 0.1 | 700 | 30 |

Example 7

This example exhibits the synergistic effect of the combination of docetaxel and the compound A wherein docetaxel and the compound A were administered sequentially such that docetaxel was administered prior to the compound A. The human non-small cell lung carcinoma H-460 cells were seeded at a density of 3000 cells/well. The cells were first treated with either of the drugs alone i.e. with docetaxel or the compound A alone. Docetaxel treatment was for the first 3 hours followed by complete medium for 45 hours while in case of the compound A treatment, the first 3 hours was in complete medium followed by the compound A for the next 45 hours. The concentrations of docetaxel used were 0.1 nM and 3 nM while the compound A was used at a concentration of 1000 nM (~$IC_{50}$ concentration after 48 hours treatment). In the combination study, the cells were first treated with 0.1 nM or 3 nM of docetaxel for 3 hours followed by 1000 nM of the compound A for 45 hours. The plates were processed for MTS viability assay and the percent cytotoxicity was calculated as compared to control. The results are as shown in the following Table 7.

TABLE 7

| Drug treatment | Concentration of Docetaxel (nM) | Concentration of CDK inhibitor (Compound A) (nM) | % Cytotoxicity |
|---|---|---|---|
| Docetaxel | 3 | 0 | 2 |
| | 0.1 | 0 | 0 |
| CDK inhibitor (compound A) | 0 | 1000 | 35 |
| Docetaxel (3 hours) followed by CDK inhibitor (compound A) (45 hours) | 3 | 1000 | 53 |
| | 0.1 | 1000 | 52 |

Example 8

This example exhibits the synergistic effect of the combination of paclitaxel and the compound A wherein paclitaxel and the compound A were administered sequentially such that paclitaxel was administered prior to the compound A. The human non-small cell lung carcinoma H-460 cells were seeded at a density of 1500 cells/well. The cells were first treated with either of the drugs alone i.e. with paclitaxel or the compound A alone. Paclitaxel treatment was for the first 3 hours followed by complete medium for 45 hours while in case of the compound A treatment, the first 3 hours was in complete medium followed by the compound A for the next 45 hours. The concentrations of paclitaxel used were 10 nM while the compound A was used at a concentration of 700 nM (~$IC_{30}$ concentration after 48 hours treatment). In the combination study, the cells were first treated with 10 nM of paclitaxel for 3 hours followed by 700 nM of the compound A for 45 hours. After completion of the drugs treatment i.e. at the end of 48 hours the plates were processed for MTS viability assay and the percent cytotoxicity was calculated as compared to control. The results are as shown in the following Table 8.

TABLE 8

| Drug treatment | Concentration of Paclitaxel (nM) | Concentration of the CDK inhibitor (Compound A) (nM) | % Cytotoxicity |
|---|---|---|---|
| Paclitaxel | 10 | 0 | 10 |
| CDK inhibitor (compound A) | 0 | 700 | 21 |
| Paclitaxel (3 hours) followed by CDK inhibitor (compound A) (45 hours) | 10 | 700 | 41 |

Example 9

This example exhibits the synergistic effect of the combination of gemcitabine and the compound A wherein gemcitabine and the compound A were administered sequentially such that gemcitabine was administered prior to the compound A. The cells from human pancreatic (Panc-1) cell line were seeded at a density of 1500 cells/well. The cells were first treated with either of the drugs alone i.e. with gemcitabine or the compound A alone. Gemcitabine treatment was for the first 24 hours followed by complete medium for 72 hours. While in case of the compound A treatment, the first 24 hours was in complete medium followed by the compound A for the next 72 hours. Gemcitabine was used at a concentration of 70 nM while the compound A was used at a concentration of 300 nM (~$IC_{30}$ concentration after 48 hours treatment). In the combination study, the cells were first treated with 70 nM of gemcitabine for 24 hours followed by 300 nM of the compound A for 72 hours. After completion of the drugs treatment i.e. at the end of 96 hours the plates were processed for MTS viability assay and the percent cytotoxicity was calculated as compared to control. The results are as shown in the following Table 9.

TABLE 9

| Drug treatment | Concentration of gemcitabine (nM) | Concentration of the CDK inhibitor (compound A) (nM) | % Cytotoxicity |
|---|---|---|---|
| Gemcitabine | 200 | 0 | 78 |
| | 100 | 0 | 38 |
| | 70 | 0 | 18 |
| | 30 | 0 | 2 |
| CDK inhibitor (compound A) | 0 | 300 | 34 |
| Gemcitabine (24 hours) followed by the CDK inhibitor (compound A) (72 hours) | 200 | 300 | 97 |
| | 100 | 300 | 82 |
| | 70 | 300 | 74 |
| | 30 | 300 | 53 |

Analysis of Cell Cycle Distribution and Flow Cytometry:

The human non-small cell lung carcinoma H-460 was seeded in 25 mm³ tissue culture flasks. After 24 hours, cells were treated with the compound A alone for 72 hours or 96 hours and the cytotoxic antineoplastic agent, doxorubicin alone for 24 hours. For the combination studies, the cells were treated first with the cytotoxic antineoplastic agent, doxorubicin for 24 hours followed by the compound A for 72 hours or 96 hours after removal of the cytotoxic antineoplastic agent and washing of the cells twice with PBS. The control cells were left untreated for 96 hours or 120 hours. Both detached and adherent cells were harvested at different time points. The cells were washed twice with approximately 5 mL of PBS with centrifugation at 1000 rpm for 10 minutes. The cells were re-suspended in 500 μL of PBS and fixed in 500 μL ice-cold 70% ethanol. The fixed cells were incubated at room temperature for 30 minutes, spun at 1000 rpm for 10 minutes. To the cell pellet 1 mL of chilled 70% ethanol was added and the cell pellet was then kept in fridge till further analysis. Cells were washed twice with PBS to remove fixative and re-suspended in 250 μL PBS. To this 50 μL of propidium iodide (4 mg/mL in PBS) and 12.5 μL Rnase A (1 mg/mL) was added. After incubation at 37° C. for 30 minutes, cells were analyzed using flow cytometry.

A Becton Dickinson FACS Calibur flow cytometer was used in accordance with the manufacturer's recommendations. The argon ion laser set at 488 nm was used as an excitation source. Cells with DNA content between 2n and 4n were designated as being in $G_1$, S and $G_2$/M phases of the cell cycle, as defined by the level of red fluorescence. Cells exhibiting less than 2n DNA content were designated as sub-$G_1$ cells. The number of cells in each cell cycle compartment was expressed as a percentage of the total number of cells present Example 10

This example gives the cell cycle distribution for the various treatments as shown in FIG. 1. About 1-2×10⁶ cells were seeded in a tissue culture flask for the treatment groups. The assay protocol was as mentioned above in "analysis of cell cycle distribution and flow cytometry". The cell cycle was divided in four parts, which are represented in the FIG. 1 as M1, M2, M3 and M4. M1 corresponds to the G1 phase, M2 to the S phase, M3 to the G2-M phase and M4 to the sub G1 phase, which represents the cells undergoing apoptosis. The 96 hour control where there was no drug treatment showed negligible apoptosis of only 2%, while the treatment group with either drug alone showed only 10% apoptosis for both the compound A and doxorubicin alone. The combination of both the drugs showed an increased apoptosis of 34%.

Example 11

Figure 2:
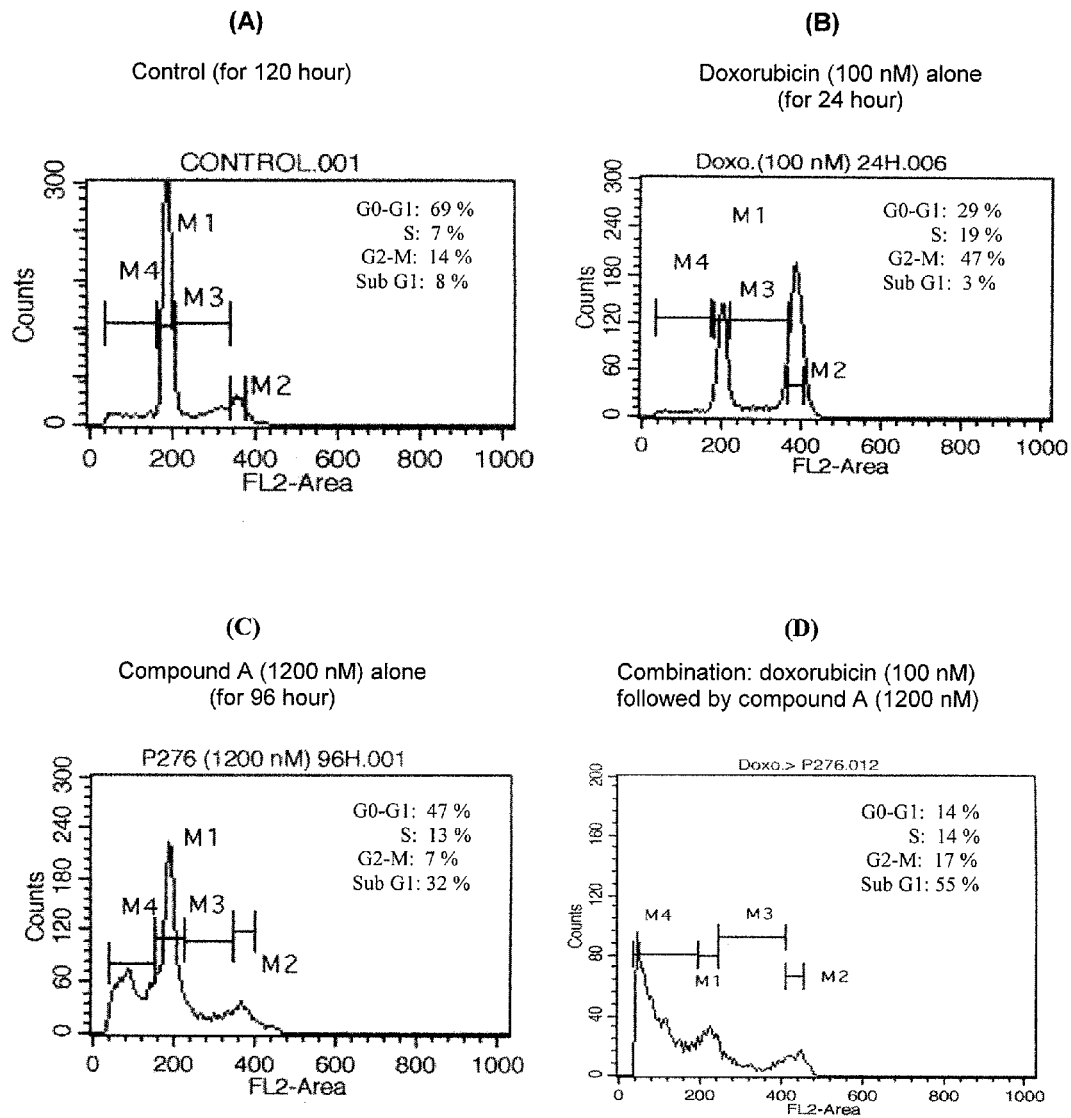
FIG. 2 illustrates that the combination of doxorubicin and the compound A in the treatment of H-460 non-small cell lung cells in vitro exhibits synergism. Graph(s) A, B, C and D represent(s) cell cycle distribution of different treatment groups namely the control (for 120 hours), 100 nM of doxorubicin alone (for 24 hours), 1200 nM of the compound A alone (for 96 hours) and the combination comprising administration of 100 nM of doxorubicin (24 hours) followed by 1200 nM compound A (96 hours) respectively.

This example gives the cell cycle distribution for the various treatment groups as shown in FIG. 2. About 1-2×10⁶ cells were seeded in a tissue culture flask for the treatment groups. The assay protocol was as mentioned above in "analysis of cell cycle distribution and flow cytometry". The cell cycle was divided in four parts, which are represented in the figure as M1, M2, M3 and M4. M1 corresponds to the G1 phase, M2 to the S phase, M3 to the G2-M phase and M4 to the sub G1 phase, which represents the cells undergoing apoptosis. The 120 hour control where there was no drug treatment showed negligible apoptosis of only 8%, while the treatment group with either drug alone showed 32% and 3% apoptosis for compound A and doxorubicin respectively. The combination of both the drugs showed an increased apoptosis of 65%.

Example 12

Figure 3:
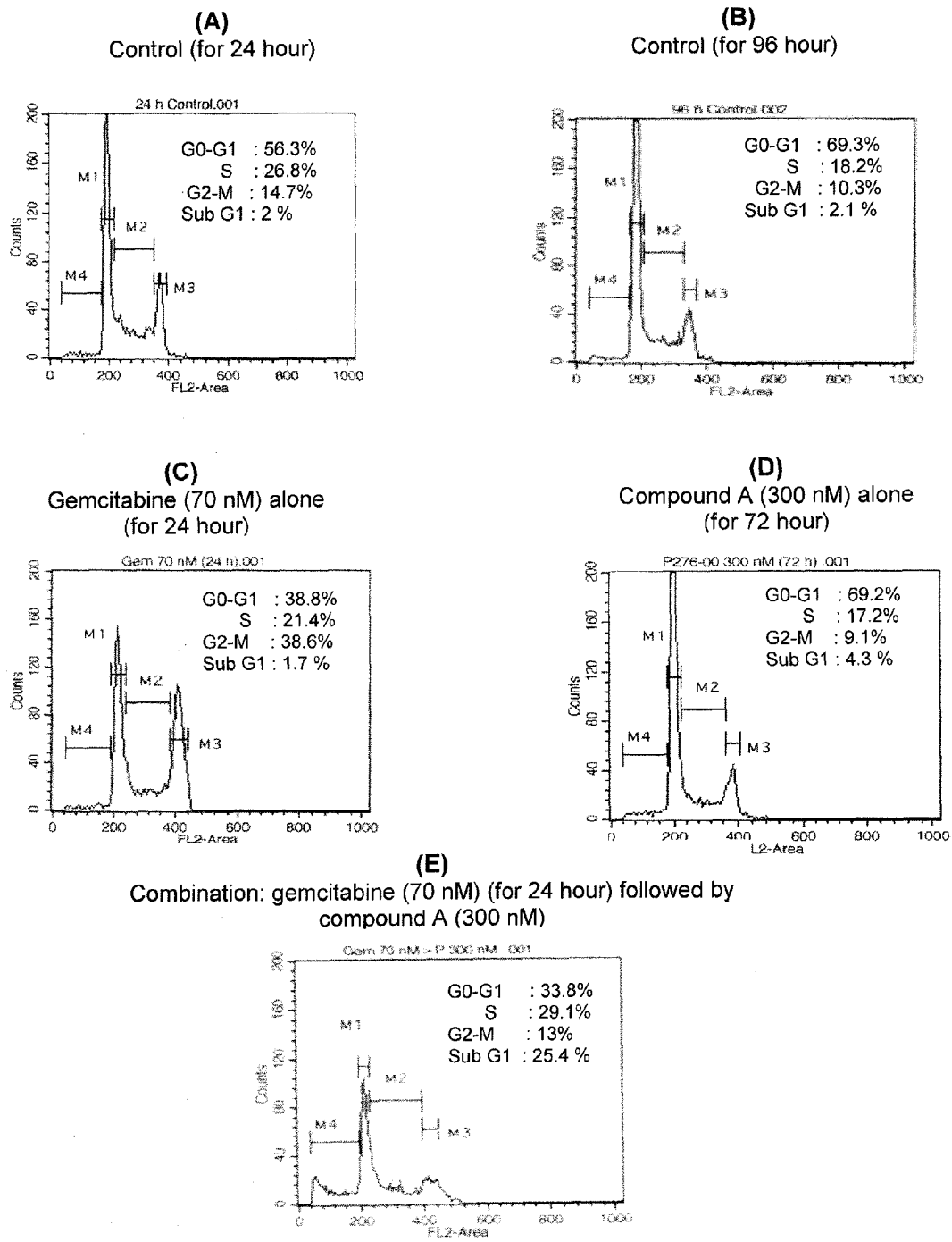
FIG. 3 demonstrates that use of the combination of gemcitabine and the compound A in the treatment of pancreatic (Panc-1) cells in vitro resulted in synergistic activity. Graph(s) A, B, C, D and E show(s) cell cycle distribution of different treatment groups namely the control (for 24 hours), the control (for 96 hours), 70 nM gemcitabine alone (for 24 hours), 300 nM of the compound A alone (for 72 hours) and the combination comprising administration of 70 nM of gemcitabine (24 hours) followed by 300 nM compound A (72 hours) respectively.

This example gives the cell cycle distribution for the various treatment groups as shown in FIG. 3. About 1-2×10⁶ pancreatic cells (Panc-1) were seeded in a tissue culture flask for the treatment groups. The assay protocol was as mentioned above in "analysis of cell cycle distribution and flow cytometry". The cell cycle was divided in four parts, which are represented in the figure as M1, M2, M3 and M4. M1 corresponds to the G1 phase, M2 to the S phase, M3 to the G2-M phase and M4 to the sub G1 phase, which represents the cells undergoing apoptosis. The 96 hour control where there was no drug treatment showed negligible apoptosis of only 2.1%, while the treatment group with either drug alone showed 4.3% and 1.7% apoptosis for compound A and gemcitabine respectively. The combination of both the drugs showed an increased apoptosis of 25.4%.

Example 13

Annexin V-FITC Staining (for the Detection of Early Apoptosis)

Annexin V-FITC is a sensitive probe for identifying apoptotic cells. During early apoptosis the membrane phospholipid phosphotidyl serine (PS) is translocated from the inner to the outer leaflet of the plasma membrane, thereby exposing PS to the external cellular environment. Annexin V is a 35-36 kDa Calcium phospholipid binding protein that has a high affinity for PS and binds to cells with exposed PS. Propidium iodide (PI) is a polar dye that enters cells through leaky membranes and hence used in conjunction with FITC for detection of late apoptosis.

The human non-small cell lung carcinoma H-460 was seeded in 25 mm³ tissue culture flasks. After 24 hours, cells were treated with 1200 nM of the compound A or 100 nM of doxorubicin alone for 96 hours and 24 hours respectively. For the combination studies cells were treated first with 100 nM of the cytotoxic antineoplastic agent, doxorubicin for 24 hours followed by 1200 nM of the compound A for 96 hours after removal of the cytotoxic antineoplastic agent (doxorubicin) and washing of the cells once with medium. The control cells were left untreated for 120 hours. Medium containing floating cells were collected and pooled with the adherent cells after harvesting with trypsin at the different time points. The cells were washed twice with cold PBS with centrifugation at 1000 rpm for 10 minutes. The cell pellet was resuspended in 1× binding buffer (10 mm HEPES pH 7.4, 140 mM NaCl, 2.5 mM $CaCl_2$) at a concentration of 1×10⁶ cells/mL. 100 μl of the solution (1×10⁵ cells) were stained with Annexin V-FITC and Propidium Iodide. The cells were incubated for 15 minutes at room temperature in the dark and the sample was analysed by flow cytometry.

Figure 4:
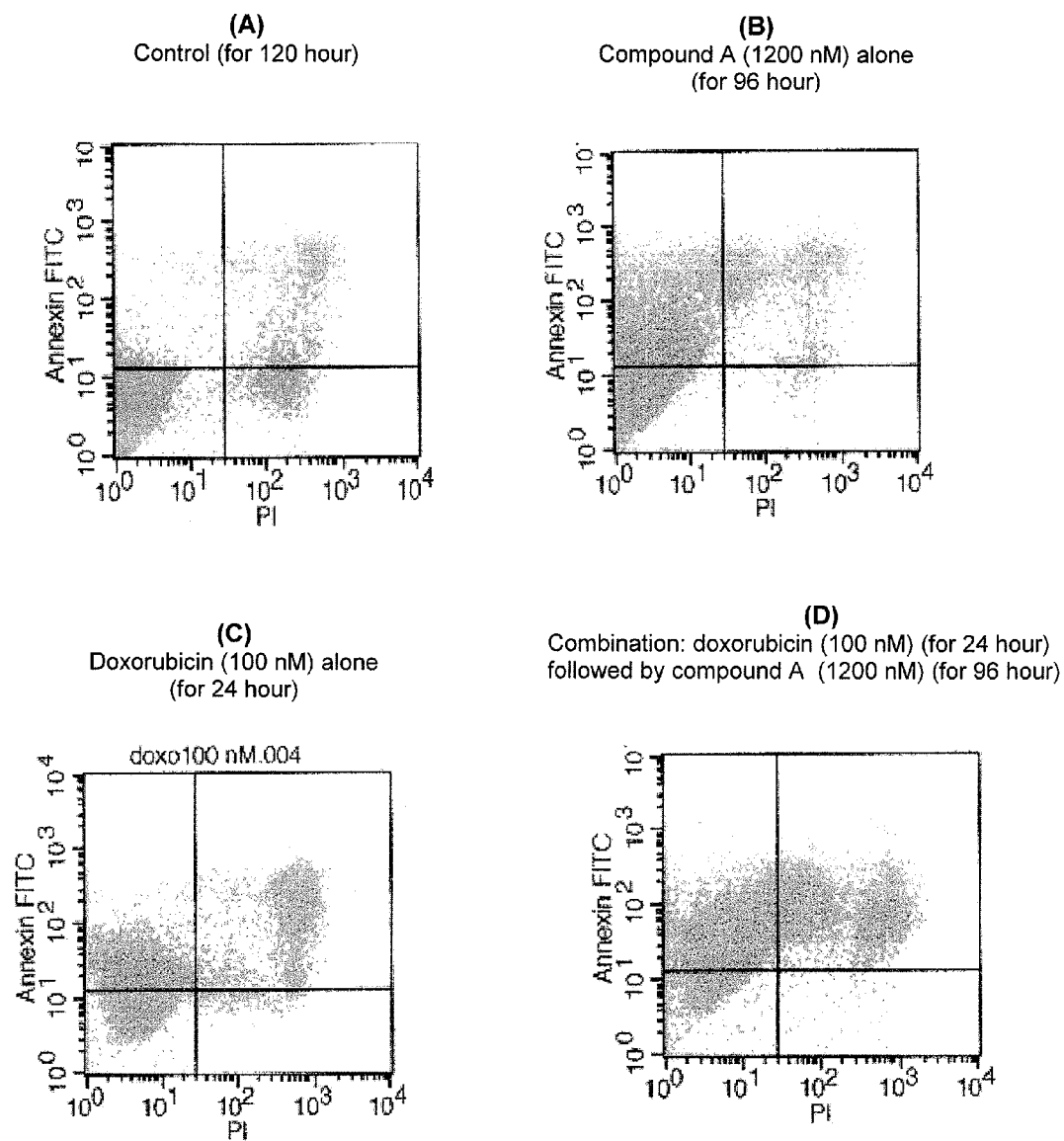
FIG. 4 demonstrates the detection of an early apoptosis in the synergistic combination of doxorubicin followed by compound A at the end of 120 hours of treatment using Annexin V staining. Graph(s) A, B, C and D show(s) the distribution of cells in four quadrants in different treatment groups namely the control (for 120 hours), 1200 nM of the compound A alone (for 96 hours), 100 nM of doxorubicin alone (for 24 hours) and the combination comprising administration of 100 nM of doxorubicin (24 hours) followed by 1200 nM compound A (96 hours) respectively

A Becton Dickinson FACS Calibur flow cytometer was used for these studies in accordance with the manufacturer's recommendations. The argon ion laser set at 488 nm was used as an excitation source. FIG. 4 shows the distribution of cells in four quadrants. Quadrant 1 situated on the lower left hand corner (LL) show cells, which are FITC and PI negative indicating that the cells are healthy. Quadrant II situated on the lower right (LR) are cells, which are positive only for PI indicating that these cells are completely apoptotic. Quadrant III on the Upper Right (UR) are cells which are positive for both annexin and PI indicating that these cells are entering from early apoptosis into late apoptosis. Quadrant IV on the upper Left (UL) shows cells that are only annexin positive, indicating that these cells are in early apoptosis. If the cells even after the termination of compound exposure continue to go into apoptosis, they would stain positive for annexin. The cells once in early apoptosis are committed to programmed cell death and at a point of no return. The results are as indicated in Table 10. It was found that the highest percentage of cells in the combination are either in early or early to late apoptosis as compared to either drug alone.

TABLE 10

| Drug treatment | Live cells (%) (healthy cells) | Annexin + ve (%) (cells in early apoptosis) | Annexin and PI + ve (%) (cells in early to late apoptosis) | PI + ve (%) (dead cells) |
| --- | --- | --- | --- | --- |
| Control | 90.5 | 3 | 4 | 2.3 |
| Doxorubicin (100 nM) | 60 | 30.4 | 8.6 | 1 |
| CDK inhibitor (compound A) (1200 nM) | 53 | 38.5 | 8.2 | 0.3 |
| Doxorubicin followed by CDK inhibitor (compound A) | 14.1 | 58.2 | 27.3 | 1 |

Example 14

Clonogenic Assay

Human non-small cell lung carcinoma cells (H-460) were seeded at a density of 750-1000 cells per 35 mm tissue culture grade plate. Incubated overnight at 37° C. for the cells to attach to the plate. The cells were treated with the cytotoxic antineoplastic agent for 24 hours followed by washing the cells and adding fresh medium containing the compound A for 96 hours. At the end of the treatment the medium was again replaced by fresh complete medium containing 10% FCS and incubated for 7-14 days for colony formation. Once visible colonies appeared on the plate, the medium was removed and colonies were fixed with Methanol: Acetic acid mixture in the ratio of 2:1 for 5 minutes. The plates were washed with water and fixation procedure was repeated. The plates were dried and the colonies were stained with 0.1% crystal violet stain for 3-5 minutes. The plates were rinsed carefully with water, dried and the colonies were counted on the Geldoc.

Figure 5:
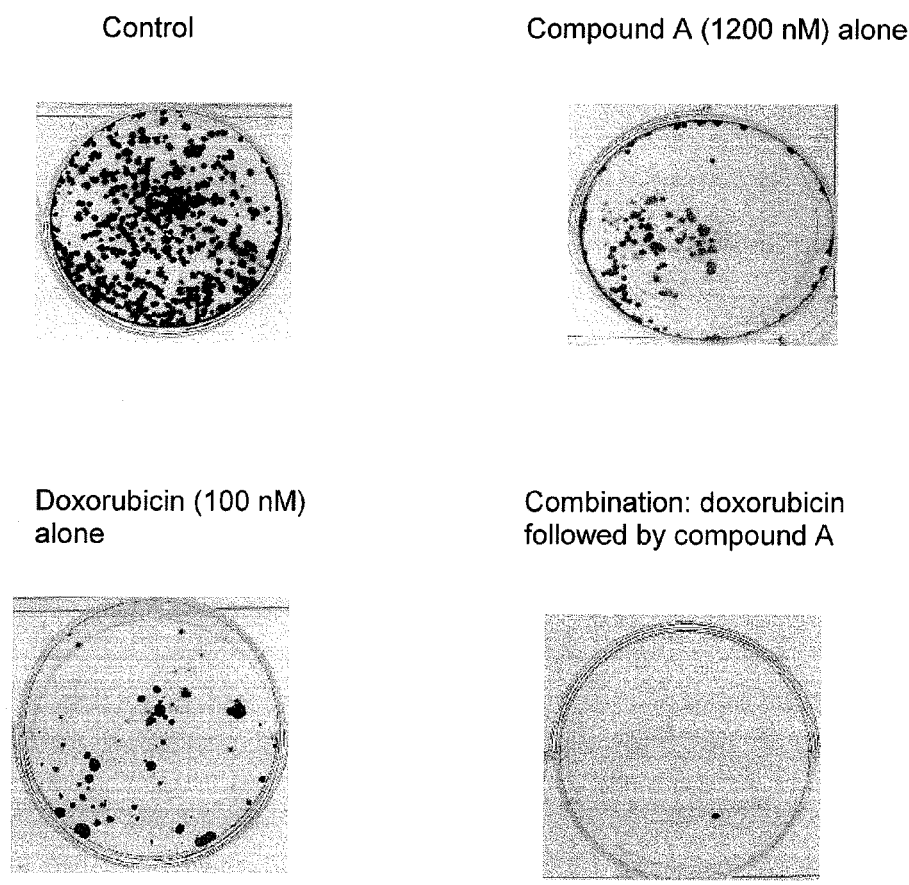
FIG. 5 illustrates that the combination of doxorubicin and the compound A in the treatment of H-460 non-small cell lung cells in vitro exhibits synergism when tested in Clonogenic assay.

The cells were treated with 1200 nM of compound A or 100 nM of doxorubicin alone for 96 hours and 24 hours respectively or in combination of 100 nM of doxorubicin followed by 1200 nM of compound A for 96 hours. FIG. 5 indicates a synergistic effect of the combination as only one colony was seen in the combination as compared to control or either of the drugs alone.

Recovery Experiments after Treatment

The assay protocol for treatment of cells with compound A and doxorubicin alone or in combination was the same as described in analysis of cell cycle distribution. Following drug treatment, the cells were allowed to recover in fresh complete medium containing 10% FCS. The cells on recovery were analyzed by FACS at 0, 6, 18, 24 and 48 hours time points for either drug alone and the combination treatment. In the following examples, the recovery of the cells is represented by the percentage of cells undergoing apoptosis.

Example 15

The cells were treated only with the cytotoxic antineoplastic agent, doxorubicin for 24 hours followed by removal of the medium and replacement with fresh complete medium. The FACS analysis was done as described in the method specified to determine the percent of cells undergoing apoptosis during the recovery period after the end of the drug treatment. The apoptosis was determined at 0, 6, 18, 24 and 48 hours during the recovery period. At the end of 24 hours of drug treatment the percent apoptosis was 3%, which during the recovery period does not increase significantly indicating that the cells ultimately recover from the drug treatment. The results are as indicated in Table 11.

TABLE 11

Recovery of cells at 0, 6, 18, 24 and 48 hours after treatment with only the cytotoxic antineoplastic agent, doxorubicin for 24 hours.

| Drug treatment (Doxorubicin 100 nM for 24 hours) | % Apoptosis |
| --- | --- |
| 0 hour recovery | 3 |
| 6 hours recovery | 5 |
| 18 hours recovery | 4 |
| 24 hours recovery | 5 |
| 48 hours recovery | 4 |

Example 16

The assay was performed as described in the protocol. The cells were treated only with the compound A for 96 hours followed by removal of medium and replacement with fresh complete medium. The FACS analysis was done as described in the method given to determine the percent of cells undergoing apoptosis during the recovery period after the end of drug treatment. The apoptosis was determined at 0, 6, 18, 24 and 48 hours during the recovery period. At the end of 96 hours of the drug treatment the percent apoptosis was 32%, which during the recovery period decreases from 24% to 19% at the end of 48 hours of recovery, indicating that the cells are gradually recovering with increase in the period of recovery. The results are as indicated in Table 12.

TABLE 12

Recovery of cells at 0, 6, 18, 24 and 48 hours after treatment with only compound A for 96 hours

| Drug treatment (Compound A 1200 nM for 96 hours) | % Apoptosis |
| --- | --- |
| 0 hour recovery | 32 |
| 6 hours recovery | 24 |
| 18 hours recovery | 23 |
| 24 hours recovery | 21 |
| 48 hours recovery | 19 |

Example 17

The assay was performed as described in the protocol. The cells were treated with doxorubicin for 24 hours followed by compound A for 96 hours followed by removal of the medium and replacement with fresh complete medium. The FACS analysis was done as described in the method given to determine the percent of cells undergoing apoptosis during the recovery period after the end of drug treatment. The apoptosis was determined at 0, 6, 18, 24 and 48 hours during the recovery period. At the end of drug treatment the percent apoptosis was 55%. During the recovery period additional 32% enter apoptosis at the end of 6 hours, which increases, to 57% at the end of 48 hours of recovery, indicating that the cells do not recover but instead continue to undergo apoptosis during the recovery period. The results are as indicated in Table 13.

TABLE 13

Recovery of cells at 0, 6, 18, 24 and 48 hours after treatment with doxorubicin for 24 hours followed by compound A for 96 hours.

| Drug treatment (Doxorubicin 100 nM for 24 hours followed by Compound A 1200 nM for 96 hours) | % Apoptosis |
|---|---|
| 0 hour recovery | 55 |
| 6 hours recovery | 32 |
| 18 hours recovery | 34 |
| 24 hours recovery | 49 |
| 48 hours recovery | 57 |

Example 18

Western Blot Analysis

Human non-small cell lung carcinoma (H-460) cells were either untreated i.e. control cells or treated with 100 nM of doxorubicin alone for 24 hours or with 1200 nM of the compound A alone for 96 hours. In the combination treatment, the cells were first treated with 100 nM of doxorubicin for 24 hours followed by 1200 nM of the compound A for 96 hours. At the end of the treatment period cells were lysed and protein content of the lysate was estimated using the Bradford reagent. 40 µg of protein was loaded on SDS-PAGE and transferred on PVDF membrane. The membranes were probed with p53, Bax, Bcl-2, cyclin D1, Cdk1 and actin antibodies. The primary antibody were detected with horseradish peroxide secondary antibody and subjected to west pico chemiluminescence reagents.

Figure 6:
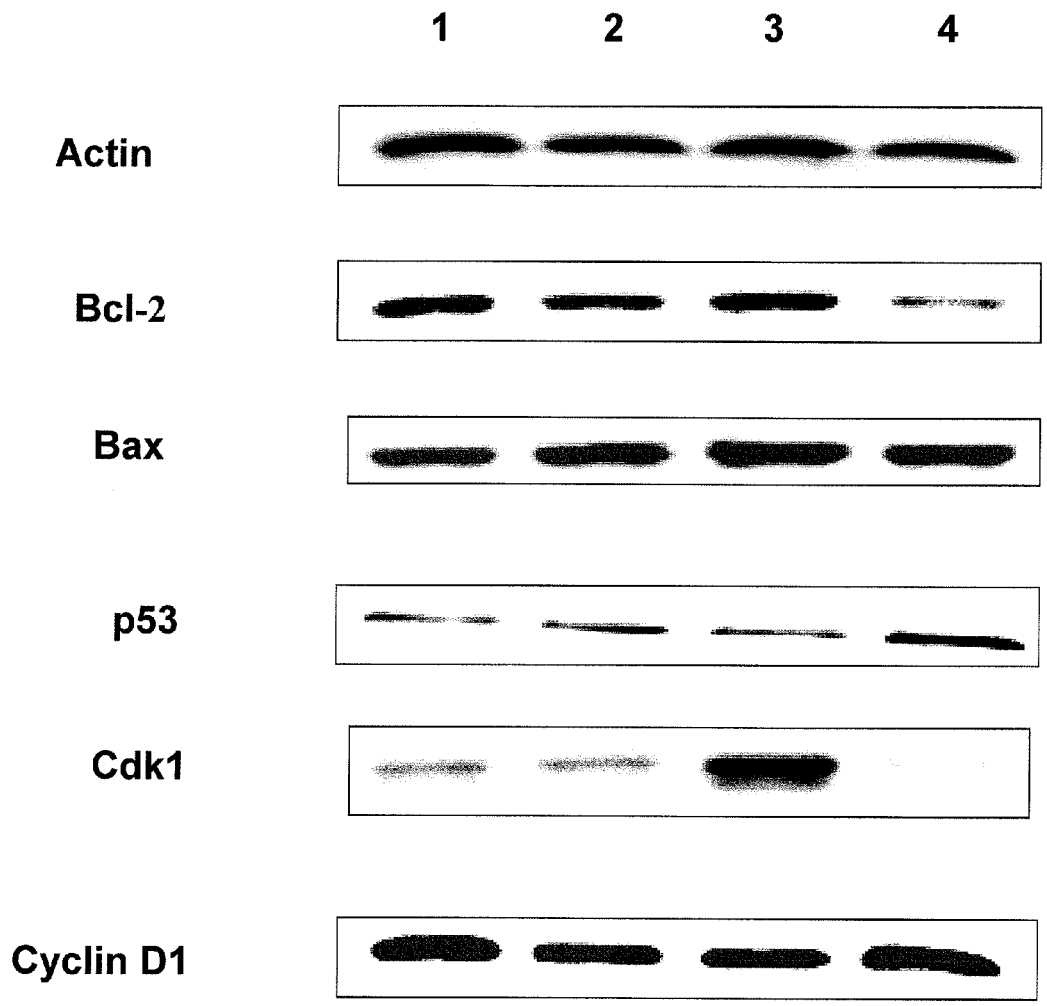
FIG. 6 shows western blot analysis of various proteins involved in the cell cycle regulation and apoptosis.

FIG. 6 shows the western blot analysis of the various proteins involved in cell cycle regulation and apoptosis. Equal amount of protein was loaded in the four lanes. The different samples loaded in the wells are described in the figure legend. The results indicate that the antiapoptotic protein Bcl-2 was significantly down regulated in the combination treatment as compared to either drug alone that was almost equivalent to the control. This correlates with the increased apoptosis seen in the combination treatment in FACS analysis. The pro-apoptotic protein Bax is slightly up regulated with respect to control in all treatment samples. The tumor suppressor protein p53 was significantly up regulated in the combination treatment as compared to control but not as much in the other two treatment group. Cdk1-B1 is an initiator of mitosis. The deregulation of this enzyme leads to tumorigenesis. Therefore inhibiting Cdk1 will inhibit its activity and hence initiation of mitosis and cell proliferation. The figure indicates that doxorubicin significantly induces Cdk1 levels while the addition of compound A reduces Cdk1 to negligible levels thus preventing the cells to go into mitosis. Compound A alone showed levels equal to control. Cyclin D1 levels do not show significant change in the various treatment groups. In the combination treatment the levels were equivalent to control while in compound A and doxorubicin alone slight reduction in the levels were seen.

Example 19

This example exhibits the in vivo efficacy testing of the combination of doxorubicin and the CDK inhibitor, the compound A in non-small cell lung (H-460) xenograft model.

Human non-small cell lung carcinoma (H-460) cell line obtained from American Type Culture Collection (ATCC), USA, was used for this study. Doxorubicin and the compound A for i.p. administration was prepared by dissolving the compounds in saline.

A group of 36 Severely Combined Immune-Deficient SCID male mice weighing ~20 g of 6-8 weeks old were used.

Human non-small cell lung carcinoma (H-460) cells were grown in RPMI 1640 medium containing 10% fetal calf serum in 5% $CO_2$ incubator at 37° C. Cells were pelleted by centrifugation at 1000 rpm for 10 minutes. Cells were resuspended in saline to get a count of $25 \times 10^6$ cells per mL, 0.2 mL of this cell suspension was injected by subcutaneous (s.c.) route in SCID mice. Mice were observed every alternate day for palpable tumor mass. Once the tumor size reached a size of 5-7 mm in diameter, animals were randomized into respective treatment groups as indicated in the following Table 14. Doxorubicin was administered once every week while the compound A was administered once every day for 5 days as indicated in Table 15. The first dose of doxorubicin was followed by the compound A after an interval of 6 hr, followed by the compound A everyday over a period of five days which comprised of one cycle. After a gap of two days the next cycle would begin. The treatment comprised of total 2 cycles. Body weight was recorded everyday. Tumor size and other signs of toxicity were recorded on every alternate day. No significant weight loss or signs of morbidity were seen. Tumor weight (mg) was estimated according to the formula for a prolate ellipsoid: $\{Length (mm) \times [width (mm)^2] \times 0.5\}$ assuming specific gravity to be one and π to be three. Tumor growth in compound treated animals was calculated as T/C (Treated/Control)×100% and Growth inhibition Percent (GI %) was [100-T/C %]. The results are graphically presented in FIGS. 7a, 7b, 8 and 9.

TABLE 14

Treatment groups

| Groups | Drug treatment | Dose | Route | No. of treatments | n= |
|---|---|---|---|---|---|
| I | Control (Untreated) | — | i.p. | | 8 |
| II | Doxorubicin | 2 mpk | i.p. | Once a week (2 w) | 8 |
| III | Compound A | 20 mpk | i.p. | Five days a week (2 w) | 8 |
| IV | Compound A | 35 mpk | i.p. | Five days a week (2 w) | 8 |
| V | Doxo > Compound A | 2 mpk > 20 mpk | i.p. | Five days a week (2 w) | 8 |
| VI | Doxo > Compound A | 2 mpk > 35 mpk | i.p. | Five days a week (2 w) | 8 |

Doxo—doxorubicin, w—week, i.p. Interperitoneally
">" indicates that doxorubicin is administered prior to the compound A.

TABLE 15

Dosing Cycle (One cycle)

| Groups | Description | M | T | W | T | F |
|---|---|---|---|---|---|---|
| Group I | Untreated | S | S | S | S | S |
| Group II | Doxorubicin 2 mpk | D | — | — | — | — |
| Group III | Compound A 20 mpk | P | P | P | P | P |
| Group IV | Compound A 35 mpk | P | P | P | P | P |

TABLE 15-continued

| | | Dosing Cycle (One cycle) | | | | |
|---|---|---|---|---|---|---|
| Groups | Description | M | T | W | T | F |
| Group V | D > P: 2 mpk > 20 mpk | D/P | P | P | P | P |
| Group VI | D > P: 2 mpk > 35 mpk | D/P | P | P | P | P |

S—Saline, P—Compound A, D—Doxorubicin
M, T, W, T and F: Days of the week (Monday, Tuesday, Wednesday, Thursday and Friday)
">" indicates that doxorubicin is administered prior to the compound A.

Example 20

Western Blot Analysis Using COX-2 Antibody

Figure 9:
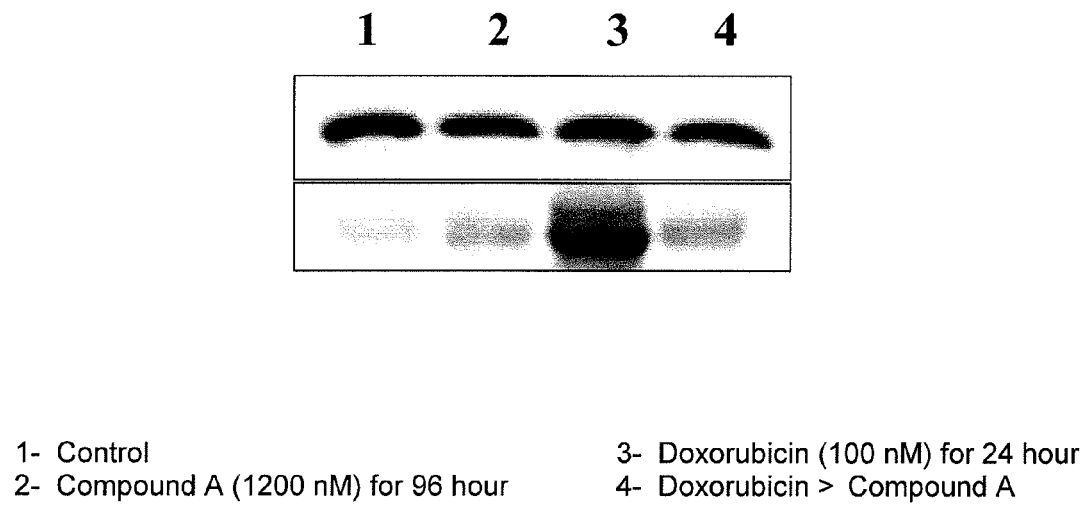
FIG. 9 shows western blotting using COX-2 antibody.

FIG. 9 indicates western blot analysis using COX-2 antibody. The different samples loaded in the wells are described in the figure legend. The results indicate that:
  Control showed basal levels of COX-2, which are low.
  The compound A alone also showed low levels of COX-2.
  Doxorubicin strongly induced COX-2 which is responsible for chemoresistance via NFκB signaling pathway.
  Addition of compound A after doxorubicin significantly down-regulated COX-2.
Therefore, NFκB mediated inhibition of COX-2 by the compound A could be involved in suppressing tumor growth and doxorubicin induced chemoresistance in human non-small cell lung carcinoma (H-460) tumor xenograft.

Example 21

Combination Studies of Doxorubicin and Flavopiridol in Human Non-Small Cell Lung Carcinoma Cell Line (H-460)

This example shows that there is no synergistic effect when flavopiridol was administered after (Table 16A), before (Table 16B) or concomitantly (Table 16C) with the cytotoxic antineoplastic agent, doxorubicin. The human non-small cell lung carcinoma H-460 cells were seeded at a density of 1500 cells/well. As per Table 16A the cells were first treated with either of the drugs alone i.e. with doxorubicin or flavopiridol alone. Doxorubicin treatment was for the first 24 hours followed by complete medium for 96 hours while in case of flavopiridol, the first 24 hours was in complete medium followed by flavopiridol for the next 96 hours. The concentrations of doxorubicin used were 30 nM, 70 nM, 100 nM and 200 nM while flavopiridol was used at a concentration of 200 nM and 350 nM ($IC_{30}$ and $IC_{50}$ concentrations respectively after 48 hours treatment). In the combination study, the cells were first treated with 30 nM, 70 nM, 100 nM and 200 nM doxorubicin for the first 24 hours followed by 200 nM and 350 nM of flavopiridol for 96 hours. After completion of the drugs treatment i.e. at the end of 120 hours the plates were processed for MTS viability assay and the percent cytotoxicity was calculated as compared to control. The results are as shown in Table 16A.

As per Table 16B the cells were first treated with either of the drugs alone i.e. with doxorubicin or flavopiridol alone. Flavopiridol treatment was for the first 96 hours followed by complete medium for 24 hours while in case of doxorubicin, the first 96 hours was in complete medium followed by doxorubicin for 24 hours. The concentrations of doxorubicin used were 30 nM, 70 nM, 100 nM and 200 nM while flavopiridol was used at a concentration of 200 nM and 350 nM (~$IC_{30}$ and ~$IC_{50}$ concentration after 48 hours treatment). In this combination study, 200 nM or 350 nM of flavopiridol was added for the first 96 hours followed by 30 nM, 70 nM, 100 nM or 200 nM of doxorubicin for 24 hours. After completion of the drugs treatment i.e. at the end of 120 hours, the plates were processed for MTS viability assay and the percent cytotoxicity was calculated as compared to control. The results are as shown in Table 16B.

Table 16C exhibits no synergistic effect of the combination of doxorubicin and flavopiridol administered simultaneously for 120 hours. The human non-small cell lung carcinoma H-460 cells were seeded at a density of 1500 cells/well. The cells were first treated with either of the drugs alone i.e. with doxorubicin or flavopiridol alone for 120 hours each. The concentrations of doxorubicin used were 30 nM, 70 nM, 100 nM and 200 nM while the flavopiridol was used at a concentration of 200 nM and 350 nM (~$IC_{30}$ and ~$IC_{50}$ concentration after 48 hours treatment). In this combination study, 30 nM, 70 nM, 100 nM or 200 nM doxorubicin and 200 nM or 350 nM of flavopiridol respectively were added together for 120 hours. After completion of the drugs treatment i.e. at the end of 120 hours the plates were processed for MTS viability assay and the percent cytotoxicity was calculated as compared to control. The results are as shown in the following Table 16C.

TABLE 16

Combination studies of Doxorubicin and Flavopiridol in H-460 cell line

A) Doxorubicin followed by CDK inhibitor, flavopiridol

| Doxo (24 h) > FP (200 nM) (96 h) | | | Doxo (24 h) > FP (350 nM) (96 h) | | |
|---|---|---|---|---|---|
| Doxo. Conc. | | % Cytotoxicity | Doxo. Conc. | | % Cytotoxicity |
| 200 nM | Doxo. | 48 | 200 nM | Doxo. | 48 |
| | Doxo. > FP | 65 | | Doxo. > FP | 75 |
| 100 nM | Doxo. | 16 | 100 nM | Doxo. | 9 |
| | Doxo. > FP | 38 | | Doxo. > FP | 66 |
| 70 nM | Doxo. | 14 | 70 nM | Doxo. | 12 |
| | Doxo. > FP | 35 | | Doxo. > FP | 71 |
| 30 nM | Doxo. | 0 | 30 nM | Doxo. | 0 |
| | Doxo. > FP | 16 | | Doxo. > FP | 56 |
| FP | 200 nM | 17 | FP | 350 nM | 57 |

TABLE 16-continued

Combination studies of Doxorubicin and Flavopiridol in H-460 cell line

B) Flavopiridol followed by doxorubicin

| FP (96 h) (200 nM) > Doxo (24 h) | | | FP (96 h) (350 nM) > Doxo (24 h) | | |
|---|---|---|---|---|---|
| Doxo. Conc. | | % Cytotoxicity | Doxo. Conc. | | % Cytotoxicity |
| 200 nM | FP > Doxo | 26 | 200 nM | FP > Doxo | 80 |
| 100 nM | FP > Doxo | 26 | 100 nM | FP > Doxo | 75 |
| 70 nM | FP > Doxo | 26 | 70 nM | FP > Doxo | 79 |
| 30 nM | FP > Doxo | 24 | 30 nM | FP > Doxo | 77 |
| FP | 200 nM | 29 | FP | 350 nM | 73 |

C) Flavopiridol and doxorubicin administered simultaneously

| Doxo + FP (200 nM) (120 h) | | | Doxo + FP (350 nM) (120 h) | | |
|---|---|---|---|---|---|
| Doxo. Conc. | | % Cytotoxicity | Doxo. Conc. | | % Cytotoxicity |
| 200 nM | Doxo. | 48 | 200 nM | Doxo. | 48 |
|  | Doxo. + FP | 68 |  | Doxo. + FP | 88 |
| 100 nM | Doxo. | 24 | 100 nM | Doxo. | 24 |
|  | Doxo. + FP | 62 |  | Doxo. + FP | 85 |
| 70 nM | Doxo. | 28 | 70 nM | Doxo. | 28 |
|  | Doxo. + FP | 65 |  | Doxo. + FP | 87 |
| 30 nM | Doxo. | 2 | 30 nM | Doxo. | 2 |
|  | Doxo. + FP | 35 |  | Doxo. + FP | 80 |
| FP | 200 nM | 39 | FP | 350 nM | 81 |

">" indicates that one drug is administered prior to the other.
Doxo = Doxorubicin, FP = Flavopiridol
"+" Indicates that the drugs are administered simultaneously.

We claim:

1. A method of treating a subject in need of treatment for pancreatic cancer, comprising:
   administering:
   a therapeutically effective amount of a cytotoxic antineoplastic agent, wherein the cytotoxic antineoplastic agent is gemcitabine or a pharmaceutically acceptable salt thereof; in combination with
   a therapeutically effective amount of a CDK inhibitor or an enantiomer or a pharmaceutically acceptable salt thereof;
   wherein said CDK inhibitor is represented by the formula:

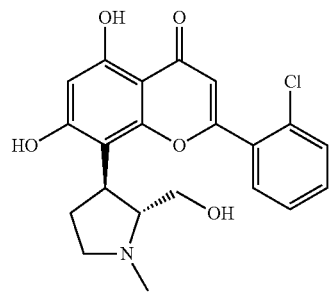 [SMILES: CN1CC[C@@H](c2c(O)cc(O)c3c(=O)cc(-c4ccccc4Cl)oc23)[C@@H]1CO]

wherein the cytotoxic antineoplastic agent is administered prior to the CDK inhibitor.

2. The method of claim 1;
   wherein the combination exhibits therapeutic synergy.

3. The method of claim 1;
   wherein the CDK inhibitor represented by compound of formula I is (+)-trans-2-(2-Chloro-phenyl)-5,7-dihydroxy-8-(2-hydroxymethyl-1-methyl-pyrrolidin-3-yl)-chromen-4-one or its pharmaceutically acceptable salt.

4. The method of claim 1;
   wherein the administration of the combination results in a synergistic increase in apoptosis.

5. The method of claim 1;
   wherein the CDK inhibitor is a compound of formula I wherein the phenyl group is substituted by 1, 2, or 3 identical or different substituents selected from:
   halogen selected from chlorine, bromine, fluorine, and iodine; and
   $C_1$-$C_4$ alkyl and trifluoromethyl.

6. The method of claim 5;
   wherein the CDK inhibitor is a compound of formula I wherein the phenyl group is substituted by 1, 2, or 3 halogens selected from chlorine, bromine, fluorine, and iodine.

7. The method of claim 6;
   wherein the CDK inhibitor is a compound of formula I wherein the phenyl group is substituted by chlorine.

* * * * *

UNITED STATES PATENT AND TRADEMARK OFFICE
CERTIFICATE OF CORRECTION

PATENT NO. : 8,822,526 B2
APPLICATION NO. : 12/600019
DATED : September 2, 2014
INVENTOR(S) : Rathos et al.

It is certified that error appears in the above-identified patent and that said Letters Patent is hereby corrected as shown below:

In the Claims:

At column 25, claim number 1, delete

" 1. A method of treating a subject in need of treatment for pancreatic cancer, comprising: administering:
    a therapeutically effective amount of a cytotoxic antineoplastic agent wherein the cytotoxic antineoplastic agent is gemcitabine or a pharmaceutically acceptable salt thereof; in combination with
    a therapeutically effective amount of a CDK inhibitor or an enantiomer or a pharmaceutically acceptable salt thereof;
wherein said CDK inhibitor is represented by the formula:

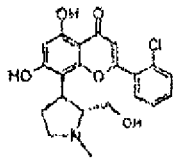

wherein the cytotoxic antineoplastic agent is administered prior to the CDK inhibitor."

And insert
--1. A method of treating a subject in need of treatment for pancreatic cancer, comprising: administering:
    a therapeutically effective amount of a cytotoxic antineoplastic agent, wherein the cytotoxic antineoplastic agent is gemcitabine or a pharmaceutically acceptable salt Signed and Sealed this
Sixteenth Day of December, 2014

Michelle K. Lee
*Deputy Director of the United States Patent and Trademark Office* thereof; in combination with a therapeutically effective amount of a CDK inhibitor or an enantiomer or a pharmaceutically acceptable salt thereof;

wherein said CDK inhibitor is represented by the following formula I;

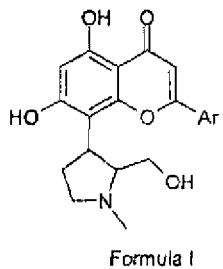

Formula I wherein Ar is phenyl, which is unsubstituted or substituted by 1, 2, or 3 identical or different substituents selected from:

halogen selected from chlorine, bromine, fluorine, and iodine; and nitro, cyano, $C_1$-$C_4$-alkyl, trifluoromethyl, hydroxyl, $C_1$-$C_4$-alkoxy, carboxy, $C_1$-$C_4$-alkoxycarbonyl, $CONH_2$, and $NR_1R_2$;

wherein $R_1$ and $R_2$ are each independently selected from hydrogen and $C_1$-$C_4$-alkyl;

wherein the cytotoxic antineoplastic agent is administered prior to the CDK inhibitor represented by the compounds of formula I.--